US010857224B2

(12) United States Patent
Martinez-Sobrido

(10) Patent No.: US 10,857,224 B2
(45) Date of Patent: Dec. 8, 2020

(54) EQUINE INFLUENZA VIRUS LIVE ATTENUATED VACCINES

(71) Applicant: University of Rochester, Rochester, NY (US)

(72) Inventor: Luis Martinez-Sobrido, Rochester, NY (US)

(73) Assignee: University of Rochester, Rochester, NY (US)

(*) Notice: Subject to any disclaimer, the term of this patent is extended or adjusted under 35 U.S.C. 154(b) by 88 days.

(21) Appl. No.: 16/306,008

(22) PCT Filed: Jun. 2, 2017

(86) PCT No.: PCT/US2017/035630
§ 371 (c)(1),
(2) Date: Nov. 30, 2018

(87) PCT Pub. No.: WO2017/210528
PCT Pub. Date: Dec. 7, 2017

(65) Prior Publication Data

US 2019/0125860 A1 May 2, 2019

Related U.S. Application Data

(60) Provisional application No. 62/345,293, filed on Jun. 3, 2016.

(51) Int. Cl.

| | |
|---|---|
| ***A61K 39/145*** | (2006.01) |
| ***A61P 31/16*** | (2006.01) |
| ***A61K 39/12*** | (2006.01) |
| ***C07K 16/10*** | (2006.01) |
| ***A61K 39/00*** | (2006.01) |

(52) U.S. Cl.
CPC ............ *A61K 39/145* (2013.01); *A61K 39/00* (2013.01); *C07K 16/1018* (2013.01); *A61K 2039/5254* (2013.01); *A61K 2039/552* (2013.01); *C12N 2760/16121* (2013.01); *C12N 2760/16134* (2013.01); *C12N 2760/16162* (2013.01)

(58) Field of Classification Search
None
See application file for complete search history.

(56) References Cited

U.S. PATENT DOCUMENTS

| | | | | |
|---|---|---|---|---|
| 7,722,884 | B2 | 5/2010 | Shields | |
| 10,478,489 | B2 | 11/2019 | Martinez-Sobrido | |
| 2011/0150912 | A1* | 6/2011 | Perez .................. | A61K 39/145 424/186.1 |
| 2018/0243401 | A1 | 8/2018 | Martinez-Sobrido | |

(Continued)

FOREIGN PATENT DOCUMENTS

| | | | |
|---|---|---|---|
| WO | 2007024947 | A2 | 3/2007 |
| WO | 2011044561 | A1 | 4/2011 |

(Continued)

OTHER PUBLICATIONS

Shinya et al. (Journal of General Virology. 2007; 88: 847-553).*

(Continued)

*Primary Examiner* — Shanon A. Foley
(74) *Attorney, Agent, or Firm* — Riverside Law LLP

(57) ABSTRACT

The present invention provides compositions and methods related to equine live-attenuated influenza vaccines.

25 Claims, 7 Drawing Sheets

Specification includes a Sequence Listing.

(56) References Cited

U.S. PATENT DOCUMENTS

2018/0256703 A1 9/2018 Martinez-Sobrido
2019/0125860 A1* 5/2019 Martinez-Sobrido ........................ C07K 16/1018
2020/0023055 A1 1/2020 Martinez-Sobrido

FOREIGN PATENT DOCUMENTS

WO 2013030176 A2 3/2013
WO 2015010073 A1 1/2015

OTHER PUBLICATIONS

Abdel-Moneim et al. (Archives of Virology. 2011; 156: 1257-1262).*
Murphy et al. (Vaccine. 1997; 15 (12/13): 1372-1378).*
Crawford et al. (Science; Oct. 2005; 310: 482-485).*
Zhou et al. (Vaccine. 2012; 30 (24): 3691-3702).*
Alignment of SEQ ID 1 of U.S. Appl. No. 16/589,247 with Geneseq db acc No. AFU64076 by Yoon et al in W02007048086 Apr. 2007, 6 pages.
Alignment of SEQ ID 1 of U.S. Appl. No. 16/589,247 with SEQ ID 1 of U.S. Pat. No. 10,478,489 Nov. 2019, 5 pages.
Alignment of SEQ ID 2 of U.S. Appl. No. 16/589,247 with SEQ ID 2 of U.S. Pat. No. 10,478,489 Nov. 2019, 5 pages.
Alignment of SEQ ID 4 of U.S. Appl. No. 16/589,247 with Geneseq db acc No. AFU64075 by Yoon et al in W02007048086 Apr. 2007, 3 pages.
Anonymous, "4 Things Pet Owners Should Know About the Dog Flu—C2CND", (Aug. 3, 2015), pp. 1-5, URL: http://c2cnd.org/connect/4-things-pet-owners-know-dog-flu/, (Oct. 27, 2016), XP055314404.
Baker et al., 2013, "Protection against lethal influenza with a viral mimic." J Virol, 87: 8591-8605.
Baker et al., 2015, "Downregulating viral gene expression: codon usage bias manipulation for the generation of novel Influenza A virus vaccines." Future Virology, 10: 715-730.
Baskin et al., 2007, "Functional Genomic and Serological Analysis of the Protective Immune Response Resulting from Vaccination of Macaques with an NS1-Truncated Influenza Virus" J Viral, 81:11817-11827.
Bean et al., 1992, "Evolution of the H3 influenza virus hemagglutinin from human and nonhuman hosts." J Virol, 66:1129-1138.
Belongia et al., 2009, "Effectiveness of inactivated influenza vaccines varied substantially with antigenic match from the 2004-2005 season to the 2006-2007 season." Journal of Infectious Diseases, 199: 159-167.
Belshe et al., 2000, "Correlates of Immune Protection Induced by Live, Attenuated, Cold-Adapted, Trivalent, Intranasal Influenza Virus Vaccine" The Journal of infectious diseases, 181:1133-1137.
Belshe et al., 2007, "Live attenuated versus inactivated influenza vaccine in infants and young children." The New England Journal of Medicine, 356: 685-696.
Bin Zhou et al, "Engineering temperature sensitive live attenuated influenza vaccines from emerging viruses", Vaccine, Elsevier Ltd, GB, vol. 30, No. 24, doi:10.1016/J.VACCINE.2012.03.025, ISSN 0264-410X, (Mar. 12, 2012), pp. 3691-3702, (Mar. 17, 2012), XP028487806.
Both et al., 1983, "Antigenic drift in influenza virus H3 hemagglutinin from 1968 to 1980: multiple evolutionary pathways and sequential amino acid changes at key antigenic sites." J Virol, 48:52, 9 pages.
Bush et al., 1999, "Positive selection on the H3 hemagglutinin gene of human influenza virus A." Molecular biology and evolution, 16: 1457-1465.
Centers for Disease Control and Prevention, 2010, "Licensure of a High-Dose Inactivated Influenza Vaccine for Persons Aged 65 Years (Fluzone High-Dose) and Guidance for Use—United States, 2010" MMWR, 59(16):485-486.
Chan et al., 2008, "The cold adapted and temperature sensitive influenza A/Ann Arbor/6/60 virus, the master donor virus for live attenuated influenza vaccines, has multiple defects in replication at the restrictive temperature." Virology, 380:304-311.
Chao, "A Single Amino Acid Deletion at the Amino Terminus of Influenza Virus Hemagglutinin Causes Malfolding and Blocks Exocytosis of the Molecule in Mammalian Cells," The Journal of Biological Chemistry, 267(4):2142-2148, 1992.
Cheng et al., 2013, The Journal of infectious diseases, 208: 594-602.
Choi et al., 2015, "Development of a dual-protective live attenuated vaccine against H5N1 and H9N2 avian influenza viruses by modifying the NS1 gene" Archives of virology, 160:1729-1740.
Communication pursuant to Article 94(3) EPC received in corresponding European Patent Application No. 16757480.5, dated Sep. 10, 2019. 11 pages.
Cox et al., 1988, "Identification of sequence changes in the cold-adapted, live attenuated influenza vaccine strain, A/Ann Arbor/6/60 (H2N2)." Virology, 167:554-567.
Cox et al., 2008, "FluBlok, a recombinant hemagglutinin influenza vaccine." Influenza and other Respiratory Viruses: 2: 211-219.
Cox et al., 2015, "Development of a mouse-adapted live attenuated influenza virus that permits in vivo analysis of enhancements to the safety of live attenuated influenza virus vaccine." J Viral, 89(6): 3421-3426.
Crawford et al., 2005, "Transmission of equine influenza virus to dogs." Science, 310: 482-485.
De Jong et al., 2007, "Antigenic and genetic evolution of swine influenza A (H3N2) viruses in Europe." J Virol, 81: 4315-4322.
De Villiers et al., 2009, "Efficacy and safety of a live attenuated influenza vaccine in adults 60 years of age and older." Vaccine, 28: 228-234.
Deshpande et al., 2009, "Evaluation of the Efficacy of a Canine Influenza Virus (H3N8) Vaccine in Dogs Following Experimental Challenge" Veterinary therapeutics: research in applied veterinary medicine, 10:103-112.
Dundon et al., 2010, "Serologic Evidence of Pandemic (H1N1) 2009 Infection in Dogs, Italy" Emerging infectious diseases, 16:2019-2021.
Epperson et al., 2013, Human infections with influenza A(H3N2) variant virus in the United States, 2011-2012. Clinical infectious diseases, 57 Suppl 1:S4-S11.
Falcon et al., 2005, "Attenuation and immunogenicity in mice of temperature-sensitive influenza viruses expressing truncated NS1 proteins" The Journal of general virology, 86:2817-2821.
Feng et al., 2015, "Equine and Canine Influenza H3N8 Viruses Show Minimal Biological Differences Despite Phylogenetic Divergence." J Viral, 89: 6860-6873.
Ferko et al., 2004, "Immunogenicity and Protection Efficacy of Replication-Deficient Influenza A Viruses with Altered NS1 Genes" J Virol, 78:13037-13045.
Garcia-Sastre et al., 1998, "Influenza A Virus Lacking the NS1 Gene Replicates in Interferon-Deficient Systems" Virology, 252:324-330.
Geiss et al., 2002, "Cellular transcriptional profiling in influenza A virus-infected lung epithelial cells: The role of the nonstructural NS1 protein in the evasion of the host innate defense and its potential contribution to pandemic influenza" Proceedings of the National Academy of Sciences, 99:10736-10741.
Gonzalez et al., 2014, "Infection and pathogenesis of canine, equine, and human influenza viruses in canine tracheas." J Viral, 88: 9208-9219.
Gorse et al., 1991, "Superiority of live attenuated compared with inactivated influenza A virus vaccines in older, Chronically ill adults." Chest, 100: 977-984.
Guo et al., 2014, "Induction of CD8 T cell heterologous protection by a single dose of single-cycle infectious influenza virus." J Viral, 88: 12006-12016.
Hai et al., 2008, "Influenza B Virus NS1-Truncated Mutants: Live-Attenuated Vaccine Approach" J Virol, 82:10580-10590.
Hale et al., 2008, "The multifunctional NS1 protein of influenza A viruses" The Journal of general virology, 89:2359-2376.
Hanson et al., "Canine Influenza," Clinicians Brief, University of Georgia, 97-103, 2016.

(56) References Cited

OTHER PUBLICATIONS

Hayward et al., 2010, "Microevolution of canine influenza virus in shelters and its molecular epidemiology in the United States." J Virol, 84:12636-12645.
Hickman et al., 2008, An avian live attenuated master backbone for potential use in epidemic and pandemic influenza vaccines. Journal of General Virology, 89(11): 2682-2690.
Holt et al., 2010, "Serologic prevalence of antibodies against canine influenza virus (H3N8) in dogs in a metropolitan animal shelter." Journal of the American Veterinary Medical Association, 237: 71-73.
Hussain et al., 2010, "Comparison of egg and high yielding MDCK cell-derived live attenuated influenza virus for commmercial production of trivalent influenza vaccine: in vitro cell susceptibility and influenza virus replication kinetics in 3emissive and semi-permissive cells." Vaccine, 28: 3848-3855.
International Search Report and Written Opinion, dated Sep. 27, 2017; recieved in PCT Application No. PCT/US2017/035630, 16 pages.
JAVMA News. 2015. Outbreak of canine influenza caused by new strain of virus. J Am Vet Med Assoc. 246:1049, 2 pages.
Jeoung et al., 2013, "A novel canine influenza H3N2 virus isolated from cats in an animal shelter." Veterinary Microbiology, 165: 281-286.
Jin et al., 2003, "Multiple amino acid residues confer temperature sensitivity to human influenza virus vaccine strains (FluMist) derived from cold-adapted A/Ann Arbor/6/60." Virology, 306: 18-24.
Jin et al., 2004, "Imparting temperature sensitivity and attenuation in ferrets to A/Puerto Rico/8/34 influenza virus by transferring the genetic signature for temperature sensitivity from cold-adapted A/Ann Arbor/6/60." J Virol, 78:995-998.
Kappes et al., 2011, "Vaccination with NS-1 truncated H3N2 swine influenza virus rimes T cells and confers cross-protection against an H1N1 heterosubtypic challenge in pigs." Vaccine, 30(2): 280-288.
Katsura et al., 2012, "A replication-incompetent virus possessing an uncleavable hemagglutinin as an influenza vaccine." Vaccine, 30: 6027-6033.
Kohlmeier et al., 2009, "Immunity to respiratory viruses." Annual review of immunology, 27: 61-82.
Lamb et al., 1980, "Mapping of the two overlapping genes for polypeptides NS1 and NS2 on RNA segment 8 of Influenza virus genome" Proceedings of the National Academy of Sciences, 77:1857-1861.
Li etal. (Infection, Genetics and Evolution. 2010; 10: 1286-1288).
Maassab, 1999, Reviews in medical virology, 9: 237-244.
Maassab., 1968, "Plaque formation of influenza virus at 25 degrees C." Nature, 219:645-646.
Mariana Baz et al., 2014, "A live attenuated H3N8 influenza vaccine is highly immunogenic and efficacious in mice and ferrets." Journal of Virology, 89(3): 1652-1659.
Martinez-Sobrido et al., 2006, "Inhibition of the type I interferon response by the nucleoprotein of the prototypic arenavirus lymphocytic choriomeningitis virus" J Viral, 80:9192-9199.
Martinez-Sobrido et al., 2009, "Identification of Amino Acid Residues Critical for the Anti-Interferon Activity of the Nucleoprotein of the Prototypic Arenavirus Lymphocytic Choriomeningitis Virus" J Virol, 83:11330-11340.
Martinez-Sobrido et al., Journal of Visualized Experiments, (2010), p. 42.
Murphy et al., "An influenza A live attenuated reassortant virus possessing three temperature-sensitive mutations in the PB2 polymerase gene rapidly loses temperature sensitivity following replication in hamsters," Vaccine, 15 (12/13):1372-1378, 1997.
Murphy et al., 2002, "Principles underlying the development and use of live attenuated cold-adapted influenza A and B virus vaccines." Viral immunology, 15: 295-323.
Newbury et al., 2016, "Prolonged intermittent virus shedding during an outbreak of canine influenza A H3N2 virus infection in dogs in three Chicago area shelters: 16 cases (Mar. to May 2015)" Journal of the American Veterinary Medical Association, 248:1022-1026.
Nogales et al., 2014, "Influenza A virus attenuation by codon deoptimization of the NS gene for vaccine development." J Viral, 88: 10525-10540.
Nogales et al., 2015, "Replication-competent influenza A viruses expressing a red fluorescent protein." Virology, 476: 206-216.
Nogales et al., 2016, "Rearrangement of Influenza Virus Spliced Segments for the Development of Live-Attenuated Vaccines." J Virol, 90: 6291-6302.
Notification of Transmittal of the International Search Report and the Written Opinion of the International Searching Authority, or the Declaration, dated Dec. 22, 2016, received in corresponding International Application No. PCT/ US2016/047715. 20 pages.
Osterholm et al., 2012, "Efficacy and effectiveness of influenza vaccines: a systematic review and meta-analysis" The Lancet Infectious Diseases, 12: 36-44.
Park et al., 2003, "Newcastle Disease Virus (NDV)-Based Assay Demonstrates Interferon-Antagonist Activity for the NDV V Protein and the Nipah Virus V, W, and C Proteins" J Virol, 77:1501-1511.
Parrish et al., 2005, "The Origins of New Pandemic Viruses: The Acquisition of New Host Ranges by Canine Parvovirus and Influenza A Viruses" Annual review of microbiology, 59:553-586.
Parrish et al., 2015, "Influenza Virus Reservoirs and intermediate Hosts: Dogs, Horses, and New Possibilities for Influenza Virus Expoure of Humans" J. Virol, 89:2990-2994.
Pecoraro et al., 2013, "Evaluation of virus isolation, one-step real-time reverse transcription polymerase chain reaction assay, and two rapid influenza diagnostic tests for detecting canine Influenza A virus H3N8 shedding in dogs." Journal of Veterinary Diagnostic Investigation, 25: 402-406.
Pica et al., 2012, "NS1-Truncated Live Attenuated Virus Vaccine Provides Robust Protection to Aged Mice from Viral Challenge" J Virol, 86:10293-10301.
Pica et al., 2013, "Toward a universal influenza virus vaccine: prospects and challenges." Annual Review of Medicine, 64: 189-202.
Powell et al., 2012, "Pseudotyped influenza A virus as a vaccine for the induction of heterotypic immunity." J Virol, 86: 13397-13406.
Pronker et al., 2012, "Development of new generation influenza vaccines: recipes for success?" Vaccine, 30: 7344-7347.
Quinlivan et al., 2005, "Attenuation of Equine Influenza Viruses through Truncations of the NS1 Protein" J Viral, 79:8431-8439.
Ramirez-Martinez et al., 2013, "Evidence of transmission and risk factors for influenza A virus in household dogs and their owners" Influenza and other respiratory viruses, 7:1292-1296.
Randall et al., 2008, "Interterons and viruses: an interplay between induction, signalling, antiviral responses and virus countermeasures" The Journal of general virology, 89:1-47.
Richt et al., 2006, "Vaccination of Pigs against Swine Influenza Viruses by Using an NS1-Truncated Modified Live-Virus Vaccine" J Viral 80:11009-11018.
Richt et al., 2009, "Attenuated Influenza Virus Vaccines with Modified NS1 Proteins" Current topics in microbiology and immunology, 333:177-195.
Rimmelzwaan et al., 2007, "Influenza virus-specific cytotoxic T lymphocytes: a correlate of protection and a basis for vaccine development" Current opinion in biotechnology, 18:529-536.
Rivailler et al., 2010, "Evolution of canine and equine influenza (H3N8) viruses co-circulating between 2005 and 2008." Virology, 408: 71-79.
Sequence alignment of SEQ ID 1 of U.S. Appl. No. 16/589,247 with Geneseq db acc No. AFB78958 by Minke et al in USPgPub2007048819 Mar. 2007, 6 pages.
Sequence alignment of SEQ ID 2 of U.S. Appl. No. 16/589,247 with Geneseq db acc No. AFB78958 by Minke et al in USPgPub2007048819 Mar. 2007, 6 pages.
Sequence alignment of SEQ ID 2 of U.S. Appl. No. 16/589,247 with Geneseq db acc No. AFU64076 by Yoon et al in W02007048086 Apr. 2007, 6 pages.
Sequence alignment of SEQ ID 3 of U.S. Appl. No. 16/589,247 with SEQ ID 3 of U.S. Pat. No. 10,478,489 Nov. 2019, 2 pages.
Sequence alignment of SEQ ID 3 of U.S. Appl. No. 16/589,247 with Geneseq db acc No. AFU64076 by Yoon et al in W02007048086 Apr. 2007, 3 pages.

(56) References Cited

OTHER PUBLICATIONS

Sequence alignment of SEQ ID 4 of U.S. Appl. No. 16/589,247 with SEQ ID 4 of U.S. Pat. No. 10,478,489 Nov. 2019, 2 pages.
Smith et al., 2009, "Origins and evolutionary genomics of the 2009 swine-origin H1N1 influenza A epidemic" Nature, 459:1122-1125.
Snyder et al., 1988, "Four viral genes independently contribute to attenuation of live influenza A/Ann Arbor/6/60 (H2N2) cold-adapted reassortant virus vaccines." J Viral, 62:488-495.
Solorzano et al., 2005, "Mutations in the NS1 Protein of Swine Influenza Virus Impair Anti-Interferon Activity and Confer Attenuation in Pigs" J Virol, 79:7535-7543.
Solorzano et al., 2010, "Alternative Live-Attenuated Influenza Vaccines Based on Modifications in the Polymerase Genes Protect against Epidemic and Pandemic Flu." Journal of Virology, 84(9): 4587-4596.
Song et al., 2007, "A New Generation of Modified Live-Attenuated Avian Influenza Viruses Using a Two-Strategy Combination as Potential Vaccine Candidates." Journal of Virology, 81(17): 9238-9248.
Song et al., 2008, "Transmission of avian influenza virus (H3N2) to dogs." Emerging Infectious Diseases, 14: 741-746.
Song et al., 2011, "Interspecies transmission of the canine influenza H3N2 virus to domestic cats in South Korea, 2010." The Journal of General Virology, 92: 2350-2355.
Song et al., 2015, "Canine susceptibility to human influenza viruses (A/pdm 09H1N1, A/H3N2 and B)." The Journal of General Virology, 96: 254-258.
Steel et al., 2009, "Live Attenuated Influenza Viruses Containing NS1 Truncations as Vaccine Candidates against H5N1 Highly Pathogenic Avian Influenza" J Virol 83:1742-1753.
Steidle et al., 2010, "Glycine 184 in Nonstructural Protein NS1 Determines the Virulence of Influenza A Virus Strain PR8 without Affecting the Host Interferon Response" J Viral, 84:12761-12770.
Su et al. (Journal of Clinical Microbiology. May 2014; 52 (5): 1762-1765).
Subbarao et al., 1995, "Sequential addition of temperature-sensitive missense mutations into the PB2 gene of Influenza A transfectant viruses can effect an increase in temperature sensitivity and attenuation and permits the rational design of a genetically engineered live influenza a virus vaccine." Journal of Virology, 69(10): 5969-5977.
Suzuki et al., "Amino Acid Substitutions of PB1 of Avian Influenza Viruses Influence Pathogenicity and Transmissibility in Chickens," Journal of Virology, 88(19):11130-11139, 2014.
Talon et al., 2000, "Influenza A and B viruses expressing altered NS1 proteins: A vaccine approach" Proceedings of the National Academy of Sciences, 97:4309-4314.
Uraki et al., 2013, "A novel bivalent vaccine based on a PB2-knockout influenza virus protects mice from pandemic H1N1 and highly pathogenic H5N1 virus challenges." J Viral, 87: 7874-7881.
Varghese et al., 1992, "The structure of the complex between influenza virus neuraminidase and sialic acid, the viral receptor." Proteins, 14: -327-332.
Victor et al., 2012, "A replication-incompetent PB2-knockout influenza A virus vaccine vector." J Viral, 86(8): 4123-4128.
Vincent et al., 2007, "Efficacy of intranasal administration of a truncated NS1 modified live influenza virus vaccine in swine" Vaccine 25:7999-8009.
Voorhees et al., "Spread of Canine Influenza A9H3N2) Virus, United States," Emerging Infectious Diseases, 23 (12):1950-1957, 2017.
Wang et al., 2008, "Characterization of influenza virus variants with different sizes of the non-structural (NS) genes and their potential as a live influenza vaccine in poultry" Vaccine, 26:3580-3586.
Wong et al., 2013, "Traditional and new influenza vaccines." Clinical Microbiology Reviews, 26: 476-492.
Xiangxiang Sun et al, "Evidence of avian-like H9N2 influenza A virus among dogs in Guangxi, China", Infection, Genetics and Evolution, NL, (Dec. 1, 2013), vol. 20, doi:10.1016/j.meegid.2013.10.012, ISSN 1567-1348, pp. 471-475, XP055314508.
Yen et al., 2009, "Pandemic influenza as a current threat." Current topics in microbiology and immunology, 333: 3-24.
Yoon et al., 2005, "Influenza virus infection in racing greyhounds." Emerging Infectious Diseases, 11: 1974-1976.
Zhang etal. (Virus Research. 2013; 175: 52-57.

* cited by examiner

Virus Titer (FFU/ml• [Log10])
Hours post-infection
0
1
2
3
4
5
6
7
8
9
0
12
24
48
72
WT
LAIV
Flu Avert

EQUINE INFLUENZA VIRUS LIVE ATTENUATED VACCINES

CROSS-REFERENCES TO RELATED APPLICATIONS

This application is a U.S. national phase application filed under 35 U.S.C. § 371 claiming benefit to International Patent Application No. PCT/US17/35630, filed Jun. 2, 2017, which is entitled to priority under 35 U.S.C. § 119(e) to U.S. Provisional Patent Application No. 62/345,293, filed Jun. 3, 2016, each of which application is hereby incorporated herein by reference in its entirety.

BACKGROUND OF THE INVENTION

Equine influenza, caused by equine influenza virus (EIV) H3N8, is the most common and important respiratory infectious diseases of horses. EIV is highly contagious and has the potential to spread rapidly through groups of naive horses in aerosolized droplets dispersed by coughing. EIV H3N8 infections of horses have been responsible of disrupting major equestrian events and causing significant economic loss. The equine population is highly mobile and horses travel long distances by road and air (among others) for competition and breeding purposes. When an infected horse is introduced into a susceptible population, the EIV spread can be explosive. Large outbreaks of H3N8 EIV are often associated with the congregation of horses at equestrian events. Their dispersal after the event can lead to widespread dissemination of the virus, with numerous examples around the World.

Vaccination is one of the most effective tools to prevent H3N8 EIV infections in horses and to limit its consequences. Current vaccines for the treatment of H3N8 EIV are either inefficient because they use inactivated viruses; or very limited in effectiveness, like the equine live-attenuated influenza vaccine (LAIV), because it was generated 25 years ago and not updated since then.

Thus, there is a need in the art for improved vaccines for EIV. The present invention satisfies this unmet need.

SUMMARY OF THE INVENTION

In one aspect, the present invention provides an immunological composition comprising an equine live-attenuated influenza virus, wherein the virus comprises one or more mutations in one or more of: segment 1 and segment 2 of the viral genome. In one embodiment, the composition is used for the treatment of equine influenza in a subject.

In one embodiment, the composition comprises a mutated segment 1 comprising the nucleic acid sequence set forth in SEQ ID NO: 1. In one embodiment, the composition comprises a mutated segment 2 comprising the nucleic acid sequence set forth in SEQ ID NO: 3.

In one embodiment, the virus comprises one or more mutations in segment 1, which encodes mutant PB2. In one embodiment, mutant PB2 comprises a N265S point mutation. In one embodiment, mutant PB2 comprises the amino acid sequence set forth in SEQ ID NO: 2.

In one embodiment, the virus comprises one or more mutations in segment 2, which encodes mutant PB1. In one embodiment, mutant PB1 comprises one or more of: K391E point mutation, E581G point mutation, and A661T point mutation. In one embodiment, mutant PB1 comprises a K391E point mutation, a E581G point mutation, and an A661T point mutation. In one embodiment, mutant PB1 comprises the amino acid sequence set forth in SEQ ID NO: 4.

In one embodiment, the virus comprises one or more mutations in segment 1, which encodes mutant PB2; and one or more mutations in segment 2, which encodes mutant PB1. In one embodiment, mutant PB2 comprises a N265S point mutation and mutant PB1 comprises a K391E point mutation, a E581G point mutation, and an A661T point mutation.

In one embodiment, the virus is derived from H3N8 subtype of equine influenza A virus. In one embodiment, the virus is a master donor virus (MDV) expressing mutant EIV H3N8 PB2, mutant EIV H3N8 PB1, and HA and NA of a different EIV strain.

In one aspect, the present invention provides a method of inducing an immune response against equine influenza virus in a subject. In one embodiment, the invention provides a method for treating or preventing equine influenza infection in a subject. In one embodiment, the method comprises administering to the subject an immunological composition comprising an equine live-attenuated influenza virus, wherein the virus comprises one or more mutations in one or more of segment 1 and segment 2 of the viral genome.

In one embodiment, the composition comprises a mutated segment 1 comprising the nucleic acid sequence set forth in SEQ ID NO: 1. In one embodiment, the composition comprises a mutated segment 2 comprising the nucleic acid sequence set forth in SEQ ID NO: 3.

In one embodiment, the virus comprises one or more mutations in segment 1, which encodes mutant PB2. In one embodiment, mutant PB2 comprises a N265S point mutation. In one embodiment, mutant PB2 comprises the amino acid sequence set forth in SEQ ID NO: 2.

In one embodiment, the virus comprises one or more mutations in segment 2, which encodes mutant PB1. In one embodiment, mutant PB1 comprises one or more of: K391E point mutation, E581G point mutation, and A661T point mutation. In one embodiment, mutant PB1 comprises a K391E point mutation, a E581G point mutation, and an A661T point mutation. In one embodiment, mutant PB1 comprises the amino acid sequence set forth in SEQ ID NO: 4.

In one embodiment, the virus comprises one or more mutations in segment 1, which encodes mutant PB2; and one or more mutations in segment 2, which encodes mutant PB1. In one embodiment, mutant PB2 comprises a N265S point mutation and mutant PB1 comprises a K391E point mutation, a E581G point mutation, and an A661T point mutation.

In one embodiment, the virus is derived from H3N8 subtype of equine influenza A virus. In one embodiment, the virus is a master donor virus (MDV) expressing mutant EIV H3N8 PB2, mutant EIV H3N8 PB1, and HA and NA of a different EIV strain.

In one embodiment, the subject does not have equine influenza, and wherein the method induces immunity against equine influenza. In one embodiment, the subject is infected equine influenza, and wherein the method induces a therapeutic immune response.

In one embodiment, the immunological composition is administered intranasally, intratracheally, orally, intradermally, intramuscularly, intraperitoneally, intravenously, or subcutaneously. In one embodiment, the subject is a horse.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3, comprising (FIG. 3A), 37° C. (FIG. 3B) and 39° C. (FIG. 3C). As internal control, MDCK cells were also infected with Flu Avert, the equine LAIV from Merck. Tissue culture supernatants were collected at 12, 24, 48 and 96 hours post-infection. Viral titers in tissue culture supernatants were determined by immunofocus assay (Focus Forming Units, FFU/ml) using an anti-NP monoclonal antibody (HB-65). Data represent the means and SD of the results determined in triplicate. Dotted black lines indicates the limit of detection (200 FFU/ml).

FIG. 5, comprising

DETAILED DESCRIPTION

Figure 1:
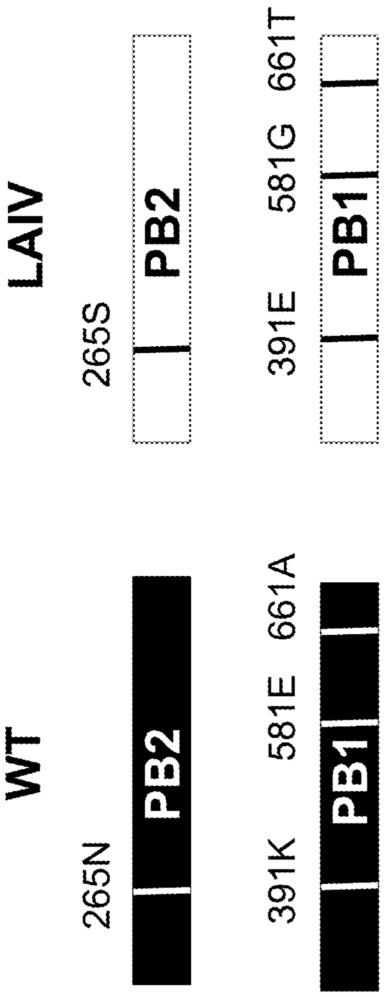
FIG. 1 depicts a schematic representation of segments 1 (PB2) and 2 (PB1) of A/equine/Ohio/1/2003 H3N8 wild-type (WT) and live-attenuated influenza virus (LAIV): Amino acid substitutions in the polymerase PB2 (N265S) and PB1 (K391E, E581G, and A661T) subunits are indicated.

The present invention relates to compositions and methods for the treatment and prevention of equine influenza virus (CIV) and EIV-related pathology. The present invention is based in part upon the discovery that various mutations in segment 1 and segment 2 of the EIV genome, thereby encoding mutant PB2 and PB1 protein, render the virus to be temperature-sensitive. For example, it is described herein that such mutations result in EIV exhibiting reduced viral replication at normal and elevated body temperature as compared to wildtype EIV. However, the temperature-sensitive EIV is able to induce a EIV-specific immune response. Thus, the temperature-sensitive EIV described herein is a live-attenuated influenza vaccine (LAIV), sometimes referred to herein as EIV LAIV. Importantly, the presently described EIV LAIV is more effective in treating EIV compared to the commercially available vaccine.

Described herein is the development of an effective and safe LAIV for the prevention and control of H3N8 EIV in horses. Reverse genetic approaches along with modifications in the viral PB2 (N265S) and PB1 (K391E, E581G, and A661T) polymerase subunits of influenza A/equine/Ohio/1/2003 H3N8 virus was used to make a cold-adapted, temperature sensitive EIV H3N8 LAIV. Compared to current inactivated vaccines, the presently described cold-adapted, temperature sensitive LAIV approach provides better and long-lasting protection against disease caused by H3N8 EIV, because LAIV induces faster and stronger production of both innate and adaptive humoral and T-cell immune responses in the target tissues of the respiratory tract. Also, in certain instances the LAIV is administered through nasal spray, which avoids the swelling and muscle soreness associated with intramuscular infections of inactivated vaccines. Moreover, in some embodiments, a single immunization with the cold-adapted, temperature sensitive LAIV is sufficient, compared to the multiple doses required with the current inactivated vaccines, to confer full protection against H3N8 EIV in a shorter period of time. Further, the present LAIV technology would provide better cross protection against antigenically different EIV H3N8 strains than that provided by the current inactivated vaccines, diminishing the chance of H3N8 EIV outbreaks.

Compared to the only available EIV H3N8 LAIV, the present technology also offers a number of advantages. The mutations introduced in the PB2 and PB1 polymerase subunits of influenza A/equine/Ohio/1/2003 H3N8 are different than those generated by cold-adaptation of the current influenza A/equine/Kentucky/1/91 H3N8 LAIV; but able to confer similar cold-adapted, temperature sensitive phenotype to the virus. Moreover, the use of state-of-the-art reverse genetic techniques facilitates, similar to the case of human LAIV, the fast and accurate development of LAIV candidates for the treatment of currently circulating Florida clade 1 and 2 subtypes, or newly introduced H3N8 EIV strains. Thus, the present LAIV approach is more effective than the currently available LAIV to treat H3N8 EIV infections in horses because of strain match. Importantly, and contrary to the current LAIV, the present cold-adapted, temperature sensitive influenza A/equine/Ohio/1/2003 H3N8 virus could be used as a master donor virus (MDV) to produce updated LAIV yearly by the introduction of HA and NA glycoproteins from antigenically different circulating EIV strains, with the final purpose being the prevention and control of currently circulating or potentially new antigenically different H3N8 equine influenza viruses in the horse population.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "normal temperature" or "normal body temperature" as used herein refers to the temperature of a healthy subject. For example, in certain instances the "normal body temperature" in a human subject is in the range of about 36° C. to about 38° C. In certain instances, in an equine subject, "normal body temperature" is in the range of about 37.5° C. to about 38.7° C.

The term "elevated temperature" or "elevated body temperature" as used herein refers to a temperature in a subject that is greater than the "normal body temperature" of a subject of a given organism. In certain instances "elevated body temperature" may be indicative of a fever, infection, or other illness. In certain instances, elevated body temperature in a human subject is greater than about 37° C. In certain instances, elevated body temperature in an equine subject is greater than about 38.9° C.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides immunological compositions and methods useful for the inhibition, prevention and treatment of equine influenza and equine influenza related diseases and disorders. In one embodiment, the immunological composition comprises a live-attenuated virus (LAV).

In one embodiment, the present invention provides a temperature-sensitive LAV of an equine influenza virus. For example, it is demonstrated herein that one or more mutations in segment 1 and/or segment 2 of the EIV genome renders the virus to be temperature-sensitive. The temperature-sensitive EIV LAIV of the present invention exhibits reduced viral replication, as compared to wildtype EIV, at both normal body temperature and at elevated or fever temperatures. However, the temperature sensitive EIV LAIV provides antigen-specific immune responses and protection against EIV. In one embodiment, the EIV LAIV provides at least the same antigen-specific immune responses and protection against EIV compared to wildtype EIV. In certain embodiments, the EIV LAIV provides greater antigen-specific immune responses and protection against EIV as compared to inactivated EIV.

In one embodiment, the composition comprises an EIV LAIV having one or more mutations in segment 1 and/or segment 2 of the viral genome. For example, in one embodiment, the EIV LAIV encodes mutant PB2 and/or mutant PB1. In certain embodiments, mutant PB2 comprises a N265S point mutation. In certain embodiments, mutant PB1 comprises at least one of a K391E point mutation, a E581G point mutation, or A661T point mutation.

In certain embodiments, the present invention provides a composition comprising a master donor virus (MDV) having one or more mutations in segment 1 and/or segment 2 of the viral genome. In one embodiment, the MDV comprises mutant H3N8 segment 1 and/or segment 2, as described herein. In certain embodiments, the MDV can be used to generate an LAIV which is protective against other pathogens. For example, in certain embodiments, an LAV against another influenza strain can be generated by using the MDV to express one or more viral proteins (e.g., HA or NA) of the other strain.

In certain embodiments, the present invention provides a method for treating or preventing EIV and EIV-related pathology, comprising administering a composition comprising an EIV LAIV. In certain embodiments, the method comprises intranasal delivery of the EIV LAIV.

In general, wild-type influenza viruses contain a segmented genome with 8 segments as described in Table 1 below:

TABLE 1

| Segment | Gene Product |
|---|---|
| 1 | PB2 (Polymerase (basic) protein 2) |
| 2 | PB1 (Polymerase (basic) protein 1) |
| 3 | PA (Polymerase (acidic) protein) |
| 4 | HA (Hemagglutinin) |
| 5 | NP (Nucleoprotein) |
| 6 | NA (Neuraminidase) |
| 7 | M1 (Matrix protein 1) and M2 (Matrix protein 2) |
| 8 | NS1 (non-structural protein 1) and NEP/NS2 (non-structural protein 2) |

In certain embodiments, the present invention provides an immunological composition comprising segment 1 and/or segment 2, wherein segment 1 and/or segment 2 comprise one or more mutations. For example, in certain embodiments, the immunological composition comprises an LAIV, comprising one or more mutations in segment 1 and/or segment 2. In one embodiment, the immunological composition comprises an EIV LAIV, comprising one or more mutations in segment 1 and/or segment 2.

The present invention also provides methods of preventing, inhibiting, and treating EIV and EIV-related diseases and disorders. In one embodiment, the methods of the invention induce immunity against EIV by generating an immune response directed to EIV. In one embodiment, the methods of the invention induce production of EIV-specific antibodies. In one embodiment, the methods of the invention prevent EIV-related pathology. In one embodiment, the methods of the invention comprise administering an immunological composition comprising a LAV, wherein the LAV comprises one or more mutations in segment 1 and/or segment 2, to a subject in need thereof. In one embodiment, the methods comprise administering an immunological composition to a subject in need thereof, thereby inducing immunity to EIV.

Compositions

The present invention provides immunological compositions that when administered to a subject in need thereof, elicit an immune response directed against equine influenza virus (EIV). In some embodiments, the composition includes polypeptides, nucleotides, vectors, or vaccines. Further, when the compositions are administered to a subject, they elicit an immune response that serves to protect the inoculated subject against equine influenza. As exemplified herein, the composition can be obtained in large quantities for use as a vaccine.

In one embodiment, the present invention provides compositions that are useful as immunomodulatory agents, for example, in stimulating immune responses and in preventing equine influenza and equine influenza-related pathology.

Live-attenuated viruses can be used as immunostimulatory agents to induce the production of EIV-specific antibodies and protect against equine influenza and equine influenza-related pathology. Therefore, in one embodiment, the composition of the invention comprises a live-attenuated EIV (EIV LAIV), wherein the EIV LAIV comprises one or more mutations in the viral genome to render the EIV LAIV temperature sensitive. For example, in one embodiment, the EIV LAIV comprises one or more mutations in segment 1 of the viral genome. The one or more mutations in segment 1 of the viral genome encode a mutant PB2 protein. In one embodiment, the EIV LAIV comprises one or more mutations in segment 2 of the viral genome. The one or more mutations in segment 2 of the viral genome encode a mutant PB1 protein. In one embodiment, the EIV LAIV comprises one or more mutations in segment 1 and one or more mutations in segment 2.

In one embodiment, the EIV LAIV is based upon the genome of Influenza A/equine/Ohio/1/2003 H3N8. Wild-type nucleic acid sequences for each segment of Influenza A/equine/Ohio/1/2003 H3N8 and wildtype amino acid sequences for the encoded proteins are summarized in Table 2 below:

TABLE 2

Wildtype sequences for Influenza A/equine/Ohio/1/2003 H3N8

| Segments | Gene Products | |
|---|---|---|
| Segment 1 (SEQ ID NO: 5) | PB2 (SEQ ID NO: 6) | |
| Segment 2 (SEQ ID NO: 7) | PB1 (SEQ ID NO: 8) | |
| Segment 3 (SEQ ID NO: 9) | PA (SEQ ID NO: 10) | |
| Segment 4 (SEQ ID NO: 11) | HA (SEQ ID NO: 12) | |
| Segment 5 (SEQ ID NO: 13) | NP (SEQ ID NO: 14) | |
| Segment 6 (SEQ ID NO: 15) | NA (SEQ ID NO: 16) | |
| Segment 7 (SEQ ID NO: 17) | M1 (SEQ ID NO: 18) | M2 (SEQ ID NO: 19) |
| Segment 8 (SEQ ID NO: 20) | NS1 (SEQ ID NO: 21) | NEP/NS2 (SEQ ID NO: 22) |

In one embodiment, the composition comprises one or more mutations in the nucleic acid sequences of segment 1, encoding PB2, and/or segment 2, encoding PB1. Thus, in certain embodiments, the composition encodes mutant PB1 and/or mutant PB2. As described herein, the one or more mutations renders the virus to be temperature-sensitive, exhibited reduced viral replication at normal or elevated temperatures.

In some embodiments, the invention provides a composition comprising one or more mutations in segment 1. For example, in one embodiment, the composition comprises segment 1 having one or more mutation which results in the production of mutant PB2 having a point mutation at amino acid residue 265. For example, in one embodiment, the mutant PB2 comprises the amino acid sequence of SEQ ID NO: 6, except having a point mutation at amino acid residue 265. For example, in one embodiment, the mutant PB2 comprises a N265S point mutation, where the mutant PB2 comprises a serine at amino acid residue 265.

In one embodiment, the composition comprises a nucleic acid sequence encoding a mutant PB2 having an amino acid sequence of SEQ ID NO: 2. In one embodiment, the composition comprises a nucleic acid sequence encoding a mutant PB2 that is substantially homologous to SEQ ID NO: 2. For example, in certain embodiments, the composition comprises a nucleic acid sequence that encodes a mutant PB2 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 2. In one embodiment, the composition comprises a nucleic acid sequence encoding a mutant PB2 that is substantially homologous to SEQ ID NO: 2, where mutant PB2 that is substantially homologous to SEQ ID NO: 2 comprises the N265S point mutation.

In one embodiment, the composition comprises a mutant segment 1 comprising the nucleotide sequence of SEQ ID NO: 1. In one embodiment, the composition comprises nucleotide sequence that is substantially homologous to SEQ ID NO: 1. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 1. In one embodiment, the composition comprises a nucleotide sequence that is substantially homologous to SEQ ID NO: 1, where the mutant PB2 encoded by the nucleotide sequence that is substantially homologous to SEQ ID NO: 1 comprises the N265S point mutation.

In some embodiments, the invention provides a composition comprising one or more mutations in segment 2. For example, in one embodiment, the composition comprises segment 2 having one or more mutation which results in the production of mutant PB1 having a point mutation at one or more of: amino acid residue 391, amino acid residue 581, and amino acid residue 661. For example, in one embodiment, the mutant PB2 comprises the amino acid sequence of SEQ ID NO: 8, except having a point mutation at one or more of: amino acid residue 391, amino acid residue 581, and amino acid residue 661. For example, in one embodiment, the mutant PB1 comprises a K391E point mutation, where the mutant PB1 comprises a glutamic acid at amino acid residue 391. In one embodiment, the mutant PB1 comprises a E581G point mutation, where the mutant PB1 comprises a glycine at amino acid residue 581. In one embodiment, the mutant PB1 comprises a A661T point mutation, where the mutant PB1 comprises a threonine at amino acid residue 661.

In one embodiment, the composition comprises a nucleic acid sequence encoding a mutant PB1 having an amino acid sequence of SEQ ID NO: 4. In one embodiment, the composition comprises a nucleic acid sequence encoding a mutant PB1 that is substantially homologous to SEQ ID NO: 4. For example, in certain embodiments, the composition comprises a nucleic acid sequence that encodes a mutant PB1 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 4. In one embodiment, the composition comprises a nucleic acid sequence encoding a mutant PB1 that is substantially homologous to SEQ ID NO: 4, where mutant PB1 that is substantially homologous to SEQ ID NO: 4 comprises one or more of the K391E point mutation, E581G point mutation, and A661T point mutation.

In one embodiment, the composition comprises a mutant segment 2 comprising the nucleotide sequence of SEQ ID NO: 3. In one embodiment, the composition comprises nucleotide sequence that is substantially homologous to SEQ ID NO: 3. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 3. In one embodiment, the composition comprises a nucleotide sequence that is substantially homologous to SEQ ID NO: 3, where the mutant PB1 encoded by the nucleotide sequence that is substantially homologous to SEQ ID NO: 3 comprises one or more of the K391E point mutation, E581G point mutation, and A661T point mutation.

In certain embodiments, the composition comprises one or more mutations in segment 1 and one or more mutations in segment 2. For example, in certain embodiments, the composition comprises segment 1 having a N265S point mutation, and segment 2 having one or more of K391E point mutation, E581G point mutation, and A661T point mutation.

In certain embodiments, the composition comprises one or more mutations in the nucleic acid sequences of segment 1 and/or segment 2, while comprising wildtype nucleic acid sequences for the rest of the segmented genome. For example, in one embodiment, the EIV LAIV comprises one or more mutations in segment 1 and comprises wildtype segment 2, segment 3, segment 4, segment 5, segment 6, segment 7, and segment 8. In one embodiment, the EIV LAIV comprises one or more mutation is segment 2 and comprises wildtype segment 1, segment 3, segment 4, segment 5, segment 6, segment 7, and segment 8. In one embodiment, the EIV LAIV comprises one or more mutations in segment 1 and segment 2 and comprises wildtype segment 3, segment 4, segment 5, segment 6, segment 7, and segment 8.

In certain embodiments, the composition comprises one or more mutations in segment 1 and/or segment 2, in combination with one or more mutations in one or more other segments of the viral genome.

In certain embodiments, the composition comprises a mutant segment 1, mutant segment 2, or combination thereof, as described herein, in combination with one or more nucleotide sequences encoding another antigen. For example, in certain embodiments, the composition comprises a mutant segment 1, mutant segment 2, or combination thereof, as described herein, in combination with one or more nucleotide sequences encoding one or more antigens of another virus or strain. For example, in certain aspects, the H3N8 EIV LAIV described herein, comprising a mutant segment 1, mutant segment 2, or combination thereof can be used as a master donor virus (MDV). For example, an MDV comprising an H3N8 comprising a mutant segment 1, mutant segment 2, or combination thereof described herein, can be modified to comprise one or more nucleotide sequences encoding one or more of PB2, PB1, PA, NP, HA, NA, M1, M2, NS1, or NEP/NS2 from another influenza strain. As such a composition comprising an H3N8 comprising a mutant segment 1, mutant segment 2, or combination thereof described herein can provide protection against a different strain, when the composition expresses an antigen of the different strain. For example, in one embodiment, a composition comprises the backbone of a H3N8 EIV LAIV comprising a mutant segment 1, mutant segment 2, or combination thereof described herein, further comprising one or more nucleotide sequences encoding one or more of PB2, PB1, PA, NP, HA, NA, M1, M2, NS1, or NEP/NS2 from another influenza strain. In one embodiment, the composition comprises the backbone of a H3N8 EIV LAIV comprising a mutant segment 1, mutant segment 2, or combination thereof described herein, further comprising one or more nucleotide sequences encoding one or more of HA or NA of a different influenza strain. For example, the composition comprising the backbone of a H3N8 EIV LAIV described herein, may be modified to express one or more viral proteins of a newly emergent strain, thereby providing protection against the newly emergent strain.

In one embodiment, the composition comprises segment 1, segment 2, segment 3, segment 5, segment 7, and segment 8 of H3N8 EIV LAIV, described herein, comprising one or more point mutations in one or more of segment 1 and segment 2, where the composition further comprises segment 4 and segment 6, of a different EIV strain.

In one embodiment, the composition comprises a mutant segment 1 of H3N8, mutant segment 2 of H3N8, or a combination thereof, further comprising segment 4, segment 6, or a combination thereof of a different EIV strain. In certain aspects, the mutant segment 1, mutant segment 2, or combination thereof of H3N8 provides for the temperature sensitive attenuated phenotype of the EIV LAIV, while the segment 4, segment 6, or combination thereof, of the different EIV strain, encodes HA, NA, or combination thereof of the different EIV strain to elicit a specific immune response to the different EIV strain in the subject.

In one embodiment, the composition comprises a plurality of EIV LAIV described herein. For example, in one embodiment, the composition comprises a first EIV LAIV, comprising mutant segment 1, mutant segment 2, or combination thereof of H3N8, where the first EIV LAIV comprises segment 4, segment 6, or a combination thereof of H3N8; and the composition further comprises a second EIV LAIV, comprising mutant segment 1, mutant segment 2, or combination thereof of H3N8, where the second EIV LAIV comprises segment 4, segment 6, or a combination thereof of a different EIV strain. In certain embodiments, the composition induces an immune response against both H3N8 and the other EIV strain.

In certain embodiments, the composition comprises a polynucleotide encoding mutant PB2 and/or mutant PB1. The polynucleotide can be RNA or DNA. In one embodiment, the composition comprises a DNA vaccine.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid comprising a nucleotide sequence having substantial homology to a nucleotide sequence of an isolated nucleic acid encoding a polypeptide disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass a RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

According to yet another embodiment, composition of the invention, comprising the nucleic acid sequences or combination of nucleic acid sequences of the present invention, is capable of generating an EIV-specific immune response. In another embodiment, the composition of the invention, comprising the nucleic acid sequences or combination of nucleic acid sequences of the present invention, is capable of generating EIV-specific antibodies. In certain embodiments, the composition is able to protect against EIV, including H3N8 EIV.

In one embodiment, the composition of the invention comprises a polypeptide, or a fragment of a polypeptide, a homolog, a variant, a derivative or a salt of a polypeptide having the sequence of any one or more of SEQ ID NO: 2 and SEQ ID NO: 4.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, composition of the invention, comprising the polypeptide or combination of polypeptides of the present invention, is capable of generating an EIV-specific immune response. In another embodiment, the composition of the invention, comprising the polypeptide or combination of polypeptides of the present invention, is capable of generating EIV-specific antibodies. In certain embodiments, the composition is able to protect against EIV, including H3N8 EIV.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

Live Attenuated Virus (LAV)

The invention relates in part to the generation, selection and identification of live attenuated viruses (LAV) that generate a EIV-specific immune response, and the use of such viruses in vaccine and pharmaceutical formulations.

As described herein, in certain embodiments the EIV LAIV comprises one or more mutations in segment 1 and/or one or more mutations in segment 2 that render the virus to be temperature-sensitive. For example, in one embodiment, the temperature-sensitive EIV LAIV exhibits reduced viral replication at normal and elevated temperatures. However, the temperature-sensitive EIV LAIV induces EIV-specific immune responses and antibody production, and is thus able to protect against EIV and EIV-related pathology.

Any mutant virus or strain which has at least one mutation can be selected and used in accordance with the invention. In one embodiment, naturally occurring mutants or variants, or spontaneous mutants can be selected that include at least one mutation in segment 1 and/or segment 2, as described elsewhere herein. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having at least one mutation in segment 1 and/or segment 2, as described elsewhere herein. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into an influenza virus, including, but not limited to H3N8 EIV using "reverse genetics" approaches. In this way, natural or other mutations which confer the attenuated phenotype can be engineered into vaccine strains. For example, deletions, insertions, or substitutions of the coding region of segment 1, encoding PB2, and/or segment 2, encoding PB1 can be engineered. Deletions, substitutions or insertions in the non-coding region of segment 1 and/or segment 2 are also contemplated. To this end, mutations in the signals responsible for the transcription, replication, polyadenylation and/or packaging of segment 1 and/or segment 2 can be engineered.

In certain instances, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. In some instances, a more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152, 845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain.

In an alternate embodiment, a combination of reverse genetics techniques and reassortant techniques can be used to engineer attenuated viruses having the desired epitopes. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

The attenuated virus of the present invention can itself be used as the active ingredient in vaccine or pharmaceutical formulations. In certain embodiments, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens.

For example, in one embodiment, the immunological composition of the invention comprises a live attenuated virus, engineered to express one or more epitopes or antigens of EIV along with epitopes or antigens of another pathogen. For example, the attenuated virus can be engineered to express neutralizing epitopes of other preselected strains. Alternatively, epitopes of other viruses can be built into the attenuated mutant virus. Alternatively, epitopes of non-viral infectious pathogens (e.g., parasites, bacteria, fungi) can be engineered into the virus.

In one embodiment, the attenuated viruses selected for use in the invention is capable of inducing a robust anti-EIV response in the host—a feature which contributes to the generation of a strong immune response when used as a vaccine, and which has other biological consequences that make the viruses useful as pharmaceutical agents for the prevention and/or treatment of other viral infections, or other diseases.

The attenuated viruses, which induce a EIV-specific immune response in hosts, may also be used in pharmaceutical formulations for the prophylaxis or treatment of other influenza infections, or influenza-related pathology. In this regard, the tropism of the attenuated virus can be altered to target the virus to a desired target organ, tissue or cells in vivo or ex vivo. Using this approach, the EIV-specific immune response can be induced locally, at the target site, thus avoiding or minimizing the side effects of systemic treatments. To this end, the attenuated virus can be engineered to express a ligand specific for a receptor of the target organ, tissue or cells.

Vaccine

In certain aspects, the immunological composition is useful as a vaccine, where the immunological composition induces an immune response to the antigen in a cell, tissue or mammal. Preferably, the vaccine induces a protective immune response in the mammal. As used herein, an "immunological composition" may comprise, by way of examples, a live-attenuated virus (LAV), an antigen (e.g., a polypeptide), a nucleic acid encoding an antigen (e.g., an antigen expression vector), or a cell expressing or presenting an antigen or cellular component. In particular embodiments the immunological composition comprises or encodes all or part of any polypeptide antigen described herein, or an immunologically functional equivalent thereof. In other embodiments, the immunological composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces anti-EIV immunity or suppresses EIV upon inoculation into an animal.

The invention encompasses vaccine formulations comprising live attenuated virus (LAV), wherein the LAV is a live attenuated equine influenza virus (referred to herein as EIV LAIV). For example, in certain embodiments, the EIV LAIV is temperature-sensitive, exhibiting reduced viral replication at normal and elevated temperatures, as compared to wildtype EIV. In one embodiment, the vaccine comprises a EIV LAIV comprising one or more mutations in segment 1 and/or segment 2, and a suitable excipient. The virus used in the vaccine formulation may be selected from naturally occurring mutants or variants, mutagenized viruses or genetically engineered viruses. Attenuated strains of EIV can also be generated via reassortment techniques, or by using a combination of the reverse genetics approach and reassortment techniques. Naturally occurring variants include viruses isolated from nature as well as spontaneous occurring variants generated during virus propagation. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

In one embodiment, the vaccine formulation comprises a plurality of mutant EIV. In one embodiment, the vaccine formulation comprises a bivalent vaccine comprising H3N8

EIV LAIV, described herein, in combination with a second LAIV, where the second LAIV is based upon the H3N8 EIV LAIV backbone but engineered to express HA and NA viral proteins of another strain.

In one embodiment, the vaccine formulation may comprise one or more of the EIV LAIV, described herein, in combination with other mutant EIV that induce an anti-EIV immune response. In one embodiment, the present invention comprises a method of generating a EIV LAIV, comprising contacting a host cell with a polynucleotide comprising the nucleic acid sequences of segment 1 and/or segment 2, having one or more mutations, described elsewhere herein.

Propagation of the virus in culture is known to persons in the art. Briefly, the virus is grown in the media compositions in which the host cell is commonly cultured. Suitable host cells for the replication of EIV include, e.g., Vero cells, BHK cells, MDCK cells, 293 cells COS cells, and CEK cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, $5^{th}$ ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of a virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Many methods may be used to introduce the vaccine formulations described above, these include but are not limited to introduction intranasally, intratracheally, orally, intradermally, intramuscularly, intraperitoneally, intravenously, and subcutaneously. It may be preferable to introduce the virus vaccine formulation via the natural route of infection of the pathogen for which the vaccine is designed, or via the natural route of infection of the parental attenuated virus.

A vaccine of the present invention, comprising an EIV LAIV, could be administered once. Alternatively, a vaccine of the present invention, comprising an EIV LAIV, could be administered twice or three or more times with a suitable interval between doses. Alternatively, a vaccine of the present invention, comprising an EIV LAIV, could be administered as often as needed to an animal, preferably a mammal.

Methods

The invention provides a method for treating or preventing equine influenza infection or an EIV-related disease or disorder. In one embodiment, the method comprises administering an immunological composition comprising a live-attenuated virus (LAV), wherein the LAV is an EIV LAIV. In one embodiment, the method comprises administering an immunological composition comprising an EIV LAIV comprising one or more mutations in segment 1 and/or segment 2, to a subject in need thereof.

As described herein, in certain embodiments, the EIV LAIV is temperature sensitive, exhibiting decreased viral replication at normal and elevated temperatures, as compared to wildtype EIV. For example, in certain embodiments, the viral replication of EIV LAIV is 2-fold less, 3-fold less, 5-fold less, 10-fold less, 15-fold less, 20-fold less, 50-fold less, 100-fold less, 500-fold less, or 1000-fold less, than wild type EIV at normal or elevated body temperature.

In certain embodiments, the EIV LAIV induces an enhanced immune response as compared to an inactivated EIV. For example, in certain embodiments, the induced immune response of EIV LAIV is 2-fold more, 3-fold more, 5-fold more, 10-fold more, 15-fold more, 20-fold more, 50-fold more, 100-fold more, 500-fold more, or 1000-fold more, than inactivated EIV. The immune response induced the EIV LAIV can be measured using standard assays. For example, in certain embodiments, the immune response induced by EIV LAIV is measured by detecting the amount of EIV-specific antibodies produced in the subject following administration of EIV LAIV.

The therapeutic compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In certain embodiments, the subject is a mammal. For example, the subject may include, but is not limited to, a human, primate, cow, horse, sheep, pig, dog, cat, or rodent. In one embodiment, the subject is a horse. The method may be used to treat or prevent EIV or EIV-related pathology in any breed or species of horse. In certain embodiments, the relative amount of active ingredient in a single dose, or the frequency of doses, will vary depending on the age, sex, weight, or breed of subject (e.g. horse).

The composition may be combined with an adjuvant. An adjuvant refers to a compound that enhances the immune response when administered together (or successively) with the immunological composition. Examples of suitable adjuvants include cholera toxin, *salmonella* toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering an immunological composition of the invention directly to a subject in need thereof. Administration of the composition can comprise, for example, intranasal, intramuscular, intravenous, peritoneal, subcutaneous, intradermal, as well as topical administration.

Furthermore, the actual dose and schedule can vary depending on whether the compositions are administered in combination with other pharmaceutical compositions, or depending on inter-individual differences in pharmacokinetics, drug disposition, and metabolism. One skilled in the art can easily make any necessary adjustments in accordance with the exigencies of the particular situation.

The regimen of administration may affect what constitutes an effective amount. The therapeutic formulations may be administered to the subject either prior to or after a diagnosis of infection or disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less.

Pharmaceutical Compositions

The present invention envisions treating or preventing EIV or EIV-related pathology in a mammal by the administration of a therapeutic composition of the invention to a mammal in need thereof. Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention encompasses pharmaceutical compositions comprising an EIV LAIV to be used as anti-viral agents or as agents against EIV-related diseases and disorders. The pharmaceutical compositions have utility as an anti-viral prophylactic and may be administered to a subject at risk of getting infected or is expected to be exposed to a virus. For example, subjects traveling to parts of the world where EIV is prevalent can be administered a pharmaceutical composition of the invention. In certain embodiments, subjects who are expected to be in contact with other subjects at risk, can be administered a pharmaceutical composition of the invention.

The EIV LAIV of the invention may be engineered using the methods described herein to express proteins or peptides which would target the viruses to a particular site. In one embodiment, where the site to be targeted expresses a receptor to a growth factor, e.g., VEGF, EGF, or PDGF, the EIV LAIV may be engineered to express the appropriate growth factor or portion(s) thereof. Thus, in accordance with the invention, the EIV LAIV may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, the pharmaceutical composition is a veterinary pharmaceutical composition suitable for administration to a veterinary subject, including but not limited to an equine subject. Exemplary equine subjects include any member of genus *equus*, including but not limited to horses, zebras, asses, and donkeys.

In certain embodiments, the veterinary pharmaceutical composition is "palatable," meaning an oral veterinary composition that is readily accepted by equines, including horses, without any coaxing or with some coaxing.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment or prevention of a particular disease or disorder will depend on the nature of the disease or disorder, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Temperature-Sensitive H3N8 EIV LAIV

Figure 2:
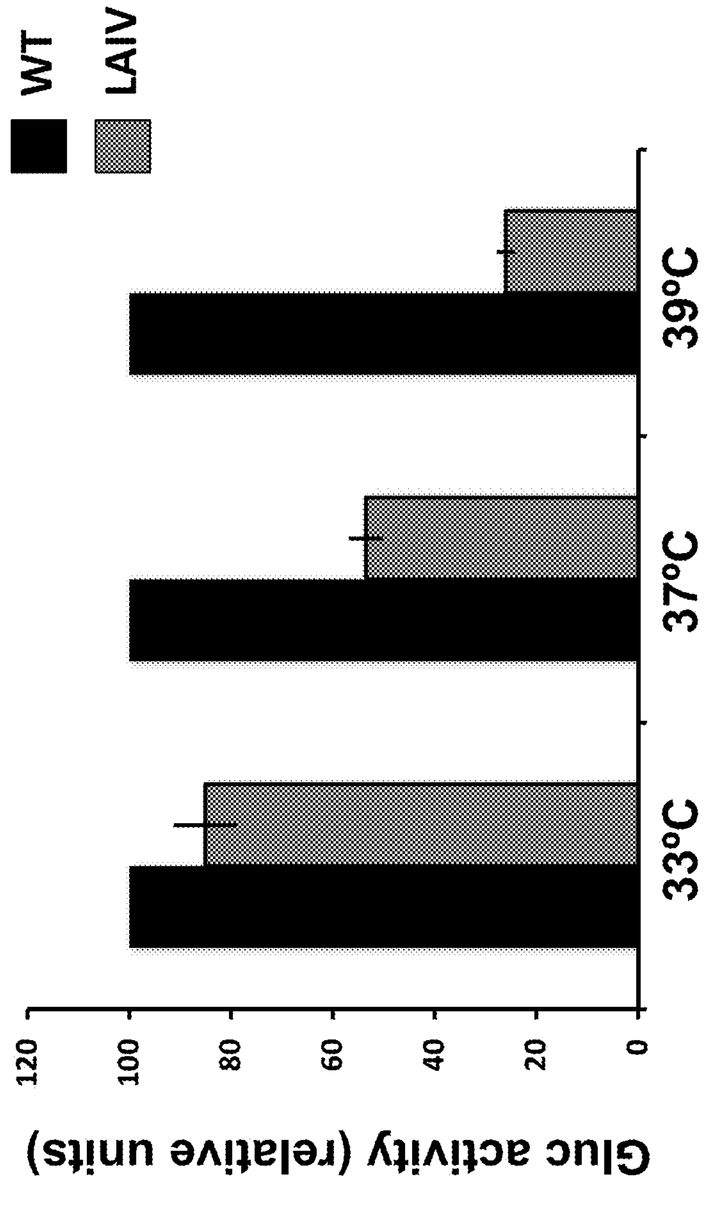
FIG. 2 depicts the results of example experiments demonstrating the effects of temperature on the polymerase activity of A/equine/Ohio/1/2003 H3N8 wild-type (WT) and live attenuated influenza virus (LAIV): Canine MDCK (12-well plate format, $6.5\times10^5$ cells/well, triplicates) were co-transfected with 200 ng of ambisense pDZ expression plasmids encoding the minimal requirements for viral replication and transcription (PB2, PB1, PA and NP), together with 500 ng of a minigenome (MG) viral (v)RNA-like expression plasmid encoding *Gaussia* luciferae (Gluc), and 100 ng of a pCAGGS constitutively expressing Cypridinia luciferase plasmid. After 6 hours, cells were placed at 33° C., 37° C. or 39° C. At 48 hours post-transfection, cells were lysed for luminescence evaluation. FFluc activity was normalized to that of *Renilla* luciferase. Data represent the means SDs of the results determined for triplicate assays. Normalized reporter expression is relative to MG activity in the absence of NP. Data are represented as relative activity considering A/equine/Ohio/1/2003 WT a 100%. Same results were obtained in equine E-Derm cells.
Figures 3A, 3B, 3C:
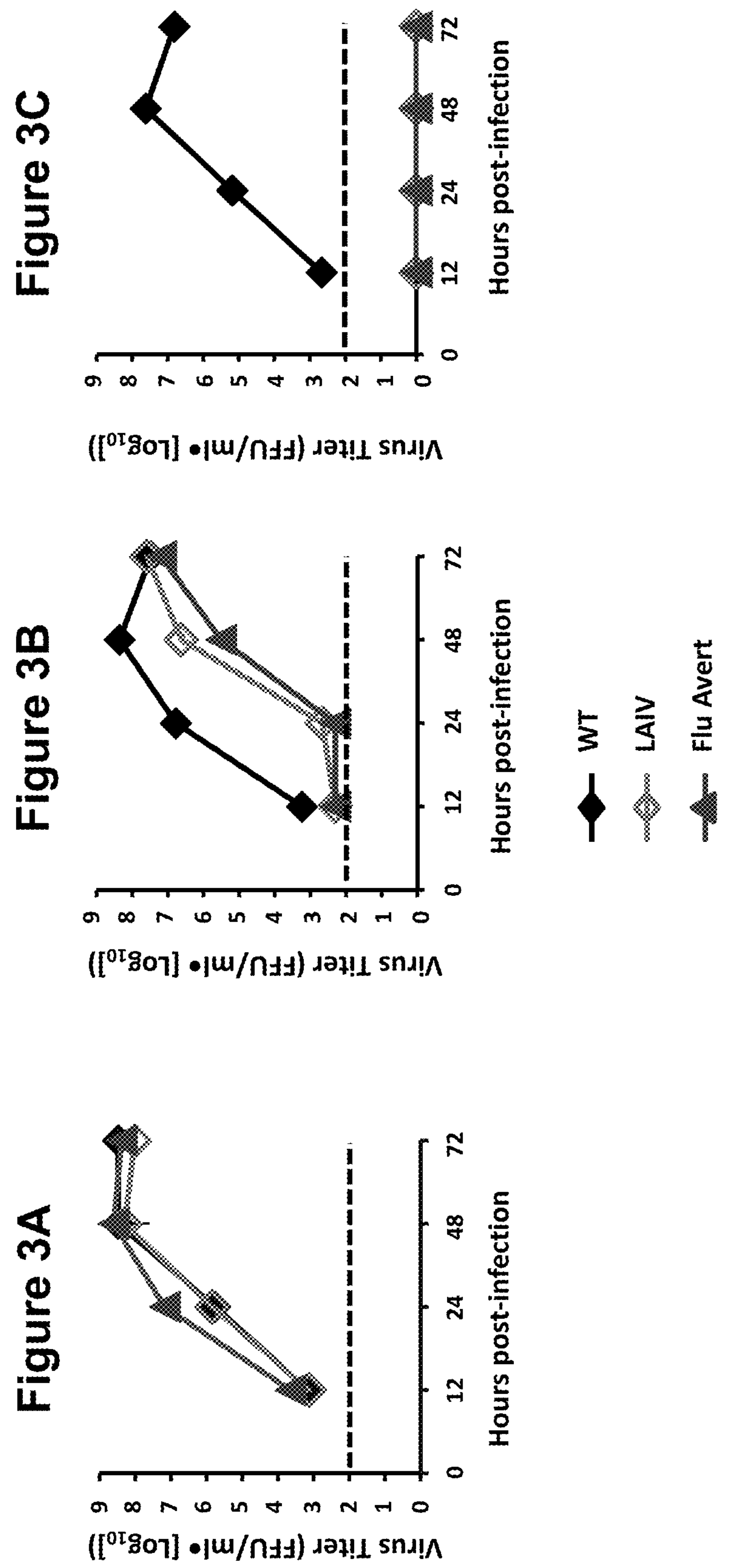
FIG. 3A through FIG. 3C, depicts the results of example experiments demonstrating the multi-cycle growth kinetics of A/equine/Ohio/1/2003 H3N8 wild-type (WT) and live-attenuated influenza vaccine (LAIV): Canine MDCK cells (12-well plate format, $6.5\times10^5$ cells/well, triplicates) were infected at low multiplicity of infection (MOI, 0.001) with A/equine/Ohio/1/2003 H3N8 WT and LAIV and incubated at 33° C.
Figure 4:
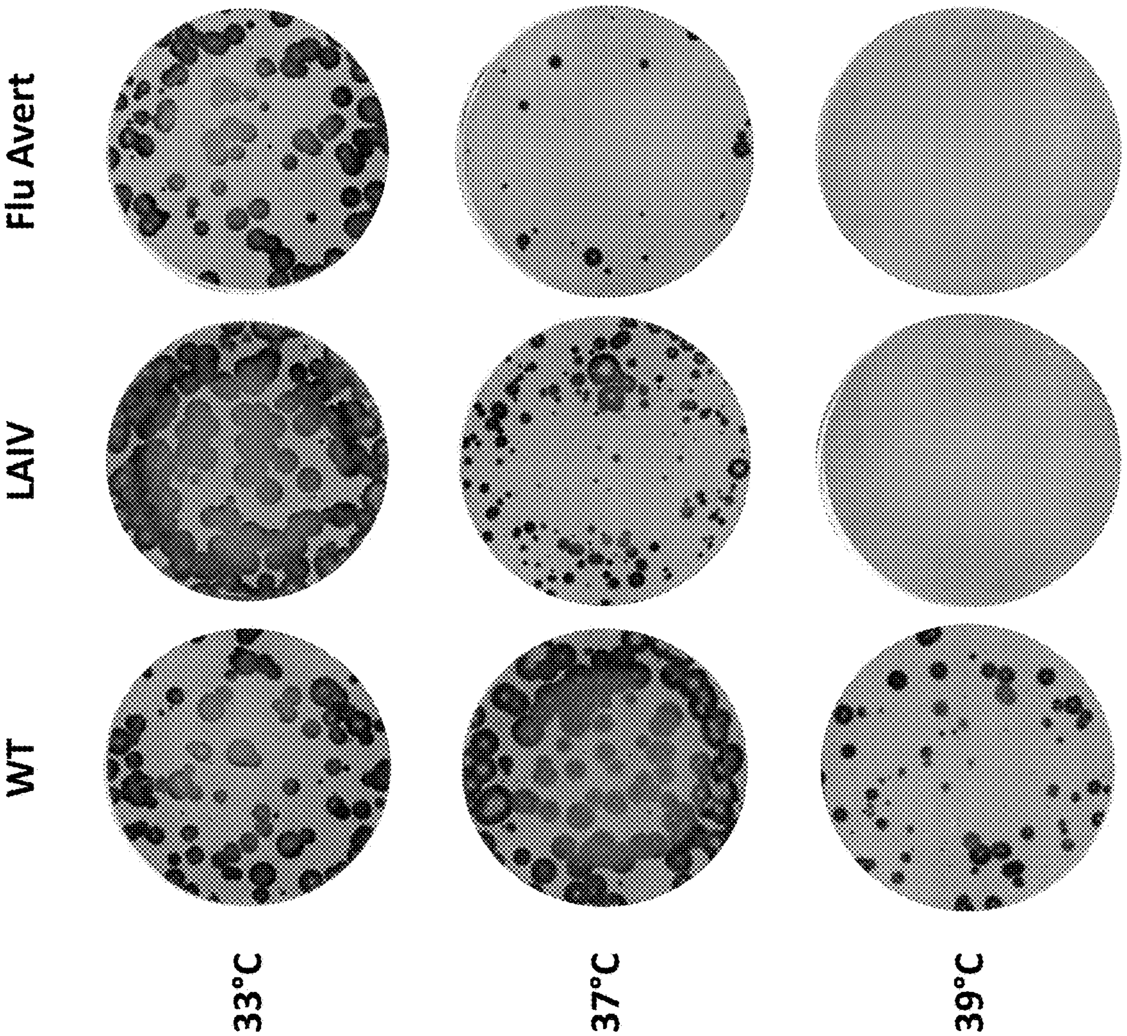
FIG. 4 depicts the results of example experiments demonstrating the effects of temperature on the plaque phenotype of A/equine/Ohio/1/2003 wild-type (WT) and live-attenuated influenza vaccine (LAIV): Canine MDCK cells (6-well plate format, $10^6$ cells/well) were infected with A/equine/Ohio/1/2003 WT and LAIV and overlaid with media containing agar. MDCK cells infected with Flu Avert were included as internal control. Three days post-infection, monolayers were immunostained with an anti-NP monoclonal antibody (HB-65).
Figure 5B:
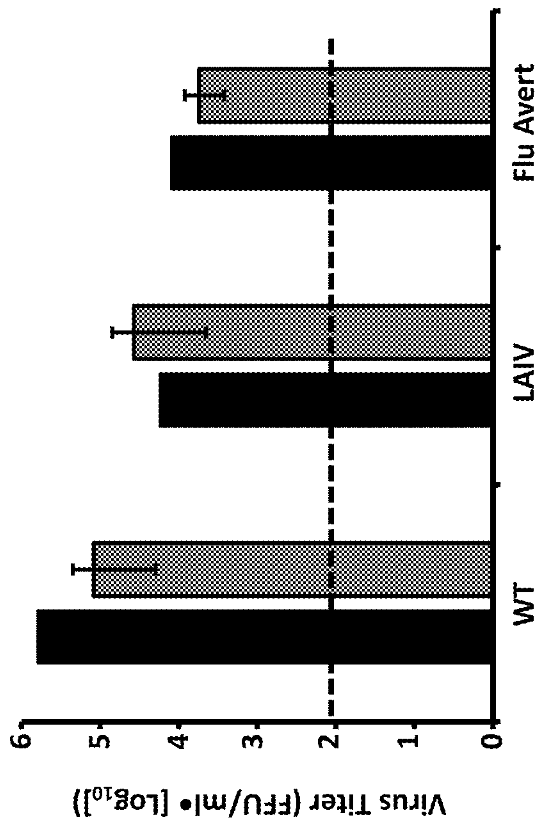
FIG. 5A and FIG. 5B, depicts the results of example experiments demonstrating the attenuation of influenza A/equine/Ohio/1/2003 H3N8 LAIV: Female 6-to-8-week-old C57BL/6 mice (N=6) were infected intranasally with $1\times10^5$ FFU of A/equine/Ohio/1/2003 H3N8 WT or LAIV, or Flu Avert as internal control. Presence of viruses in the lungs (FIG. 5A) and the nasal turbinate (FIG. 5B) of infected mice were evaluated at days 2 (N=3) and 4 (N=3) post-infection by immunofocus assay (FFU/ml) using an anti-NP monoclonal antibody (HB-65). Data represent the means and SD. Dotted black lines indicate limit of detection (200 FFU/ml).
Figure 5A:
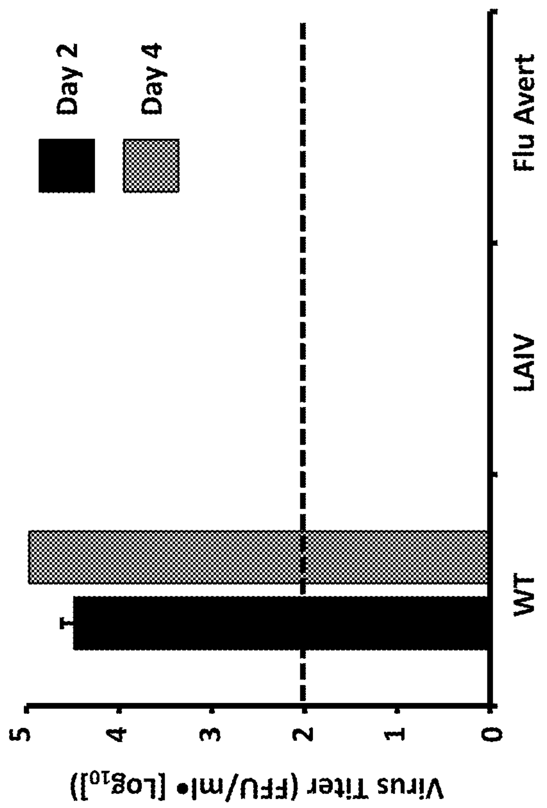
Figure 6:
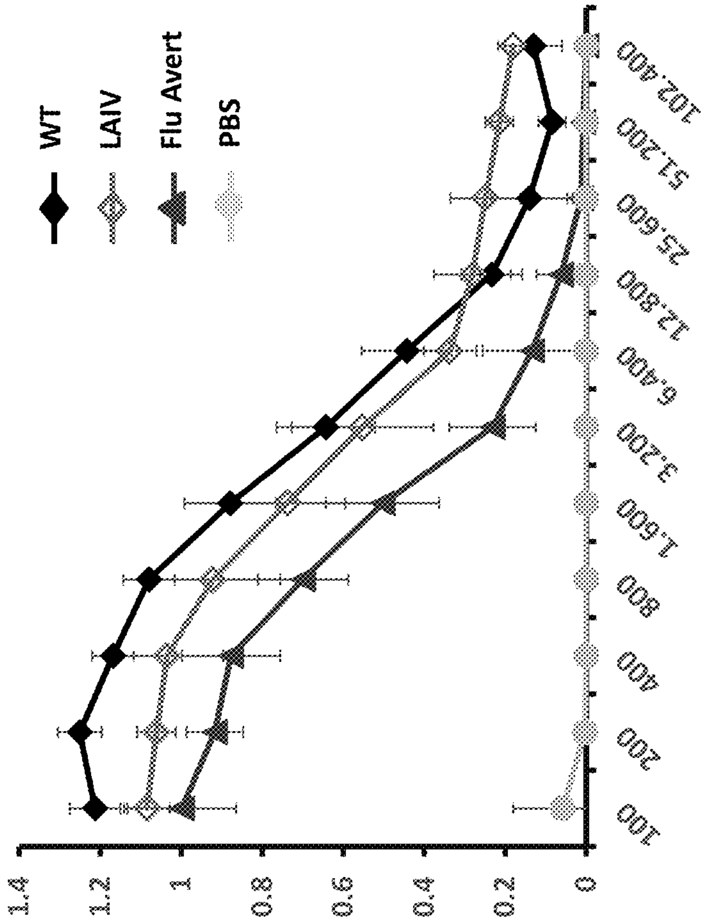
FIG. 6 depicts the results of example experiments demonstrating the induction of humoral responses by influenza A/equine/Ohio/1/2003 H3N8 LAIV: Female 6-to-8-week-old C57BL/6 mice were immunized with $1\times10^3$ FFU of A/equine/Ohio/1/2003 H3N8 WT or LAIV. Mice were also mock immunized or immunized with $1\times10^3$ FFU of Flu Avert as negative and positive controls, respectively. At 14 days post-infection, mice were bled and the sera were collected and evaluated by ELISA for IgG antibodies against total influenza virus protein using cell extracts of MDCK cells infected with A/equine/Ohio/1/2003 WT virus. Mock-infected cell extracts were used to evaluate the specificity of the antibody response. OD, optical density. Data represent the means+/−SDs of the results for 6 individual mice.
Figure 7:
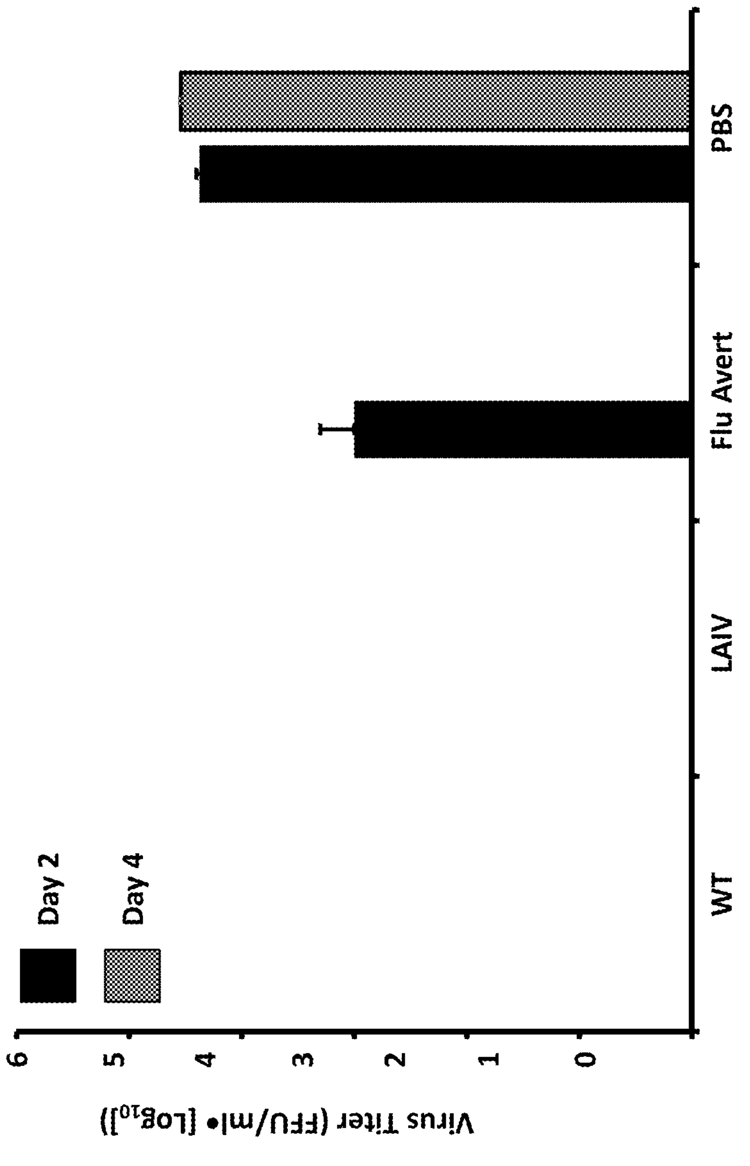
FIG. 7 depicts the results of example experiments demonstrating the protection efficacy of influenza A/equine/Ohio/1/2003 H3N8 LAIV: Female 6-to-8-week-old C57BL/6 mice (N=6) were vaccinated with $1\times10^3$ FFU of A/equine/Ohio/1/2003 H3N8 WT or LAIV. Mice were also mock vaccinated or vaccinated with $1\times10^3$ FFU of Flu Avert as negative and positive controls, respectively. Two weeks post-vaccination, mice were challenged with $1\times10^5$ FFU of influenza A/equine/Ohio/1/2003 H3N8 WT and viral titers at days 2 (N=3) and 4 (N=4) post-challenge were evaluated from lung homogenates by immunofocus assay (FFU/ml) using an anti-NP monoclonal (HB-65). Dotted black lines indicate limit of detection (200 FFU/ml). Data represent the means+/−SDs.

Using state-of-the-art plasmid-based reverse genetic approaches, a cold-adapted, temperature sensitive recombinant H3N8 equine influenza virus (EIV) live-attenuated influenza vaccine (LAIV) was generated. To generate the presently described H3N8 EIV LAIV, amino acid substitutions were introduced in the viral polymerase PB2 (N265S) and PB1 (K391E, E581G, and A661T) subunits of influenza A/equine/Ohio/1/2003 H3N8 (FIG. 1). Using a minigenome replication assay, it was found that introduction of these PB2 and PB1 mutations resulted in reduced viral genome replication and gene transcription at high (37° C.-39° C.), but not low (33° C.), temperatures (FIG. 2). These results demonstrate that amino acid substitutions in the PB2 and PB1 polymerase subunits of influenza A/equine/Ohio/1/2003 H3N8 results in a cold-adapted, temperature sensitive phenotype. It was next assessed if these mutations in the viral polymerase PB2 and PB1 subunits of influenza A/equine/Ohio/1/2003 H3N8 would result in impaired growth kinetics at restrictive (37° C.-39° C.) but not permissive (33° C.) temperatures. The replication kinetics of the cold-adapted, temperature sensitive LAIV and the wild-type influenza A/equine/Ohio/1/2003 H3N8 viruses were compared in both canine MDCK cells infected at a low multiplicity of infection (MOI, 0.001). At 33° C., both wild-type and LAIV A/equine/Ohio/1/2003 H3N8 viruses grew similarly and reached viral titers of ~$10^8$ forming focus units (FFU/ml) at the peak of infection (~48 hours post-infection). However, replication of the cold-adapted, temperature sensitive EIV LAIV was significantly reduced or impaired at 37° C. and 39° C., respectively, as compared to WT EIV (FIG. 3A-FIG. 3C). Notably, the temperature sensitivity of the presently described EIV LAIV was similar to that of the commercially available EIV LAIV Flu Avert (Merck). Moreover, the temperature sensitivity of the presently described EIV LAIV was further confirmed by plaque assay in MDCK cells (FIG. 4). These results demonstrate that mutations in the PB2 and PB1 polymerase subunits of influenza A/equine/Ohio/1/2003 H3N8 resulted in a cold-adapted, temperature sensitive phenotype, that is still able to replicate to levels comparable to WT A/equine/Ohio/1/2003 H3N8 virus at permissive (33° C.) temperatures, important for LAIV manufacturing. Experiments in mice were also conducted to evaluate the safety, immunogenicity and protection efficacy of the presently described EIV LAIV. These in vivo experiments indicate that the presently described EIV LAIV is attenuated, as compared to EIV WT, in the lower respiratory track since the presence of the EIV LAIV could not be detected in the lungs of infected ($10^5$ FFU) mouse (FIG. 5A). On the other hand, the EIV LAIV replicates better than the commercial EIV LAIV Flu Avert in the nasal mucose of infected mice (FIG. 5B). Notably, the presently described EIV LAIV induced similar humoral responses (FIG. 6), including neutralizing antibodies (Table 3), than those induced by infection with EIV WT and higher than those of the current EIV LAIV Flu Avert. Importantly, a single intranasal immunization with the presently described EIV LAIV conferred complete protection against a challenge with EIV WT (FIG. 7). Notably, protection was better than that obtained with Flu Avert.

TABLE 3

Protective humoral response: Presence of neutralizing antibodies using a conventional Hemagglutination Inhibition (HAI) assay. HAI titers from mice vaccinated with equine influenza viruses

| Immunization and dose virus[a] | | Geometric mean (SD) serum HAI titer[b] |
|---|---|---|
| PBS | — | ≤16 (ND) |
| WT | $10^3$ | 147 |
| LAIV | $10^3$ | 141 |
| Flu Avert | $10^3$ | 101 |

[a]Virus was administered intranasally to anesthetized mice (N = 6), and sera were collected at 14 days post-infection.
[b]Eight HAU of WT influenza A/equine/Ohio/1/2003 H3B8 was incubated with 2-fold serial dilutions of the indicated sera.

In addition to the mouse studies, the safety, immunogenicity and protection efficacy of the presently described H3N8 EIV LAIV has been evaluated in horses. The data from the horse studies demonstrate that the H3N8 EIV LAIV is safe and is able to confer protection against a challenge with wild-type H3N8 EIV. The observed protection includes the lack of clinical symptoms as well as reduced levels of challenge wild-type virus at different days post-infection in vaccinated horses, while control mock-vaccinated horses developed symptoms of EIV infection (e.g. coughing and fever) and high levels of viral replication in the nasal washes at days 2-6 post-challenge. Assays are also conducted to evaluate the protective immune responses, including neutralizing antibodies, from both mock-vaccinated and vaccinated horses.

Altogether, these results demonstrate the feasibility of developing a new LAIV candidate for the treatment and control of H3N8 EIV by combining state-of-the-art plasmid-based reverse genetic approaches with the introduction of mutations in the viral PB2 (N265S) and PB1 (K391E, E581G, and A661T) polymerase subunits of A/equine/Ohio/1/2003 H3N8 to generate a cold-adapted, temperature sensitive LAIV.

Example 2: Temperature Sensitive Live Attenuated Equine Influenza Virus Based on A/Equine/Ohio/1/2003 H3N8

Mutated Segment 1 or PB2:

1. Mutated nucleotide sequence of segment 1 (PB2): In bold are indicated the nucleotide changes resulting in N265S amino acid change in PB2 protein. Underlined a ClaI restriction site introduced in the modified PB2 segment.

(SEQ ID NO: 1)
agcgaaagcaggtcaaatatattcaatatggagagaataaaagaactgag agatctgatgttacaatcccgcacccgcgagatactaacaaaaactactg tggaccacatggccataatcaagaaatacacatcaggaagacaagagaag aaccctgcacttaggatgaaatggatgatggcaatgaaatacccaatcac ggcagataagaggataatggagatgattcctgagagaaatgaacagggac aaaccctttggagcaaaacgaacgatgctggctcagaccgcgtaatggta tcacctctggcagtgacatggtggaataggaatggaccaacaacaagcac aattcattatccaaaagtctacaaaacttattttgaaaaggttgaaagat tgaaacacggaacctttggccccgttcattttaggaatcaagtcaagata agacgaagagttgatgtaaaccctggtcacgcggacctcagtgccaaaga agcacaagatgtgatcatggaagttgttttcccaaatgaagtgggagcca gaattctaacatcggaatcacaactaacaataaccaaagagaaaaaggaa gaacttcaggactgcaaaattgctcccttgatggtagcatacatgctaga aagagagttggtccgaaaaacaaggttcctcccagtagcaggcggaacaa gcagtgtatacattgaagtgttgcatctgactcagggaacatgctgggag caaatgtacaccccaggaggagaagttagaaacgatgatattgatcaaag tttaattattgcagcacg<u>atcgat</u>agtgagaagagcaacagtatcagcag atccactagcatccctactggaaatgtgccacagtacacagattggtgga ataaggatggtagacatccttaagcagaatccaacagaggaacaagctgt ggatatatgcaaagcagcaatgggattgagaattagctcatcattcagct ttggtggattcaccttcaaaagaacaagtggatcatcagtcaagagagaa gaagaaatgcttacgggcaaccttcaaacattgaaaataagaatgcatga gggctatgaagaattcacaatggtcggaagaagagcaacagctattctca gaaaggcaaccagaagattgattcaattgatagtaagtgggagagatgaa caatcaattgctgaagcaataattgtagccatggtgttttcgcaagaaga ttgcatgataaaagcagttcgaggcgatttgaactttgttaatagagcaa atcagcgtttgaaccccatgcatcaactcttgaggcatttccaaaaagat gcaaaagtgcttttccaaaattggggaattgaacccatcgacaatgtaat ggggatgattggaatattgcctgacatgaccccaagcaccgagatgtcat tgagaggagtgagagtcagcaaaatgggagtggatgagtactccagcact gagagagtggtggtgagcattgaccgtttttaagagttcgggatcaaag gggaaacatactactgtcccctgaagaagtcagtgaaacacaaggaacgg aaaagctgacaataatttattcgtcatcaatgatgtgggagattaatggt cccgaatcagtgttggtcaatacttatcaatggatcatcaggaactggga aattgtaaaaattcagtggtcacaggaccccacaatgttatacaataaga tagaatttgagccattccaatccctggtccctagggccaccagaagccaa tacagcggtttcgtaagaaccctgtttcagcaaatgcgagatgtacttgg aacatttgatactgctcaaataataaaactcctcccttttgccgctgctc ctccggaacagagtaggatgcagttctcttctttgactgttaatgtaaga ggttcgggaatgaggatacttgtaagaggcaattccccagtgttcaacta -continued caataaagccactaaaaggctcacagtcctcggaaaggatgcaggtgcgc ttactgaggacccagatgaaggtacggctggagtagaatctgctgttcta agagggtttctcattttaggtaaagaaaacaagagatatggcccagcact aagcatcaatgaactaagcaaacttgcaaaaggggagaaagccaatgtac taattgggcaaggggacgtagtgttggtaatgaaacggaaacgtgactct agcatacttactgacagccagacagcgaccaaaaggattcggatggccat caattagtgttgaattgtttaaaaacgaccttgtttctact 2. Amino acid sequence of mutant EIV PB2 protein: In bold is indicated the amino acid change N265S.

(SEQ ID NO: 2)
MERIKELRDLMLQSRTREILTKTTVDHMAIIKKYTSGRQEKNPALRMKWM

MAMKYPITADKRIMEMIPERNEQGQTLWSKTNDAGSDRVMVSPLAVTWWN

RNGPTTSTIHYPKVYKTYFEKVERLKHGTFGPVHFRNQVKIRRRVDVNPG

HADLSAKEAQDVIMEVVFPNEVGARILTSESQLTITKEKKEELQDCKIAP

LMVAYMLERELVRKTRFLPVAGGTSSVYIEVLHLTQGTCWEQMYTPGGEV

RNDDIDQSLIIAARSIVRRATVSADPLASLLEMCHSTQIGGIRMVDILKQ

MPTEEQAVDICKAAMGLRISSSFSFGGFTFKRTSGSSVKREEEMLTGNLQ

TLKIRMHEGYEEFTMVGRRATAILRKATRRLIQLIVSGRDEQSIAEAIIV

AMVFSQEDCMIKAVRGDLNFVNRANQRLNPMHQLLRHFQKDAKVLFQNWG

IEPIDNVMGMIGILPDMTPSTEMSLRGVRVSKMGVDEYSSTERVVVSIDR

FLRVRDQRGNILLSPEEVSETQGTEKLTIIYSSSMMWEINGPESVLVNTY

QWIIRNWEIVKIQWSQDPTMLYNKIEFEPFQSLVPRATRSQYSGFVRTLF

QQMRDVLGTFDTAQIIKLLPFAAAPPEQSRMQFSSLTVNVRGSGMRILVR

GNSPVFNYNKATKRLTVLGKDAGALTEDPDEGTAGVESAVLRGFLILGKE

NKRYGPALSINELSKLAKGEKANVLIGQGDVVLVMKRKRDSSILTDSQTA

TKRIRMAIN

Mutated Segment 2 or PB1:

1. Mutated nucleotide sequence of segment 2 (PB1): In bold are indicated the nucleotide changes resulting in K391E, E581G, and A661T amino acid change in PB2 protein. AatI restriction site (denoted by underline) and Hind III restriction site (denoted by underline+italics) were introduced in the modified PB1 segment. Denoted in underline+bold are nucleotide mutated from the original PB1 sequence to remove a BamHI restriction site.

(SEQ ID NO: 3)
agcgaaagcaggcaaaccatttgaatggatgtcaatccgactctactttt cttaaaggtgccagcgcaaaatgctataagcacaacattcccttatactg gagatcctccctacagtcatggaacagggacaggatacaccatggatact gtcaacagaacacaccaatattcagaaaaagggaaatggacaacaaacac tgagattggagcaccacaacttaatccaatcgatggaccacttcctgaag acaatgaaccaagtgggtacgcccaaacagattgtgtattggaagcaatg gctttccttgaagaatcccatcccggaatctttgaaaattcgtgtcttga aacgatggaggtgattcagcagacaagagtggacaaactaacacaaggcc -continued gacaaacttatgattggaccttgaataggaatcaacctgccgcaacagca cttgctaatacgattgaagtattcagatcaaatggtctgacttccaatga atcggggagattgatggacttcctcaaagatgtcatggagtccatgaaca aggaagaaatggaaataacaacacacttccaacggaagagaagagtaaga gacaacatgacaaagagaatggtaacacagagaaccatagggaagaagaa acaacgattaaacagaaagagctatctaatcagaacattaaccctaaaca caatgaccaaggacgctgagagagggaaattgaaacgacgagcaatcgct accccagggatgcagataagagggtttgtatattttgttgaaacactagc ccgaagaatatgtgaaaagcttgaacaatcaggattgccagttggcggta atgagaaaaaggccaaactggctaatgtcgtcagaaaaatgatgactaat tcccaagacactgaactctccttcaccatcactggggacaataccaaatg gaatgaaaatcagaacccacgcatattcctggcaatgatcacatacataa ctagaaaccagccagaatggttcagaaatgttctaagcattgcaccgatt atgttctcaaataaaatggcaagactggggaaaggatatatgtttgaaag caaaagtatgaaattgagaactcaaataccagcagaaatgctagcaagca ttgacctgaaatatttcaatgattcaacaaaaaagaaaattgaagaaata aggcctcttctggttgacgggactgcttcactgagtcctggcatgatgat gggaatgttcaacatgttgagcactgtgctgggtgtatccatattaaacc tgggccagaggaaatacacaaagaccacatactggtgggatggtctgcaa tcatccgatgactttgctttgatagtgaatgcgcctaatcatgaaggaat acaagctggagtagacagattctatagaacttgcaaactggtcgggatca acatgagcaaaaagaagtcctacataaatagaactggaacattcgaattc acaagctttttctaccggtatggttttgtagccaatttcagcatggaact acccagttttggggtttccggaataaatgaatctgcagacatgagcattg gagtgacagtcatcaaaaacaacatgataaataatgatctcggtcctgcc acggcacaaatggcactccaactcttcattaaggattatcggtacacata ccggtgccatagaggtgatacccagatacaaaccagaagatcttttgagt tgaagaagctttgggggcagactcgatcaaagactggtctactggtatca gatgggggtccaaacctatataacatcagaaacctacacatcccggaagt ctgtttaaaatgggagctaatggatgaagattataaggggaggctatgca atccattgaatcctttcgttagtcacaaagaaattgaatcagtcaacagt gcagtagtaatgtctgcgcatggccctgccaaaagcatggagtatgatgc tgttactacaacacattcttggatacccaagaggaaccggtccatattga acacaagccaaaggggaatactcgaagatgagcagatgtatcagaaatgc tgcaacctgtttgaaaaattcttccccagcagctcatacagaagaccagt cggaatttctagtatggttgaggccatggtgtccagggcccgcattgatg cacgaattgacttcgaatctggacggataaagaaggatgagttcgctgag atcatgaagatctgttccaccattgaagagctcagacggcaaaaatagtg aatttagcttgatcttcatgaaaaaatgccttgtttctact 2. Amino acid sequence of mutant EIV PB1 protein: In bold are indicated the amino acid changes K391E, E581G and A661T.

(SEQ ID NO: 4)

MDVNPTLLFLKVPAQNAISTTFPYTGDPPYSHGTGTGYTMDTVNRTHQYS

EKGKWTTNTEIGAPQLNPIDGPLPEDNEPSGYAQTDCVLEAMAFLEESHP

GIFENSCLETMEVIQQTRVDKLTQGRQTYDWTLNRNQPAATALANTIEVF

RSNGLTSNESGRLMDFLKDVMESMNKEEMEITTHFQRKRRVRDNMTKRMV

TQRTIGKKKQRLNRKSYLIRTLTLNTMTKDAERGKLKRRAIATPGMQIRG

FVYFVETLARRICEKLEQSGLPVGGNEKKAKLANVVRKMMTNSQDTELSF

TITGDNTKWNENQNPRIFLAMITYITRNQPEWFRNVLSIAPIMFSNKMAR

LGKGYMFESKSMKLRTQIPAEMLASIDLKYFNDSTKKKIEEIRPLLVDGT

ASLSPGMMMGMFNMLSTVLGVSILNLGQRKYTKTTYWWDGLQSSDDFALI

VNAPNHEGIQAGVDRFYRTCKLVGINMSKKKSYINRTGTFEFTSFFYRYG

FVANFSMELPSFGVSGINESADMSIGVTVIKNNMINNDLGPATAQMALQL

FIKDYRYTYRCHRGDTQIQTRRSFELKKLWOQTRSKTGLLVSDGGPNLYN

IRNLHIPEVCLKWELMDEDYKGRLCNPLNPFVSHKEIESVNSAVVMSAHG

PAKSMEYDAVTTTHSWIPKRNRSILNTSQRGILEDEQMYQKCCNLFEKFF

PSSSYRRPVGISSMVEAMVSRARIDARIDFESGRIKKDEFAEIMKICSTI

EELRRQK

Wildtype Segment 1 or PB2:

1. Nucleotide sequence of wildtype EIV H3N8 segment 1 (PB2):

(SEQ ID NO: 5)

agcgaaagcaggtcaaatatattcaatatggagagaataaaagaactgag agatctgatgttacaatcccgcacccgcgagatactaacaaaaactactg tggaccacatggccataatcaagaaatacacatcaggaagacaagagaag aaccctgcacttaggatgaaatggatgatggcaatgaaatacccaatcac ggcagataagaggataatggagatgattcctgagagaaatgaacagggac aaaccctttggagcaaaacgaacgatgctggctcagaccgcgtaatggta tcacctctggcagtgacatggtggaataggaatggaccaacaacaagcac aattcattatccaaaagtctacaaaacttattttgaaaaggttgaaagat tgaaacacggaacctttggccccgttcattttaggaatcaagtcaagata agacgaagagttgatgtaaaccctggtcacgcggacctcagtgccaaaga agcacaagatgtgatcatggaagttgttttcccaaatgaagtgggagcca gaattctaacatcggaatcacaactaacaataaccaaagagaaaaaggaa gaacttcaggactgcaaaattgctcccttgatggtagcatacatgctaga aagagagttggtccgaaaaacaaggttcctcccagtagcaggcggaacaa gcagtgtatacattgaagtgttgcatctgactcagggaacatgctgggag caaatgtacaccccaggaggagaagttagaaacgatgatattgatcaaag tttaattattgcagcacggaacatagtgagaagagcaacagtatcagcag atccactagcatccctactggaaatgtgccacagtacacagattggtgga -continued ataaggatggtagacatccttaagcagaatccaacagaggaacaagctgt ggatatatgcaaagcagcaatgggattgagaattagctcatcattcagct ttggtggattcaccttcaaaagaacaagtggatcatcagtcaagagagaa gaagaaatgcttacgggcaaccttcaaacattgaaaataagaatgcatga gggctatgaagaattcacaatggtcggaagaagagcaacagctattctca gaaaggcaaccagaagattgattcaattgatagtaagtgggagagatgaa caatcaattgctgaagcaataattgtagccatggtgttttcgcaagaaga ttgcatgataaaagcagttcgaggcgatttgaactttgttaatagagcaa atcagcgtttgaaccccatgcatcaactcttgaggcatttccaaaaagat gcaaaagtgcttttccaaaattggggaattgaacccatcgacaatgtaat ggggatgattggaatattgcctgacatgaccccaagcaccgagatgtcat tgagaggagtgagagtcagcaaaatgggagtggatgagtactccagcact gagagagtggtggtgagcattgaccgtttttaagagttcgggatcaaag gggaaacatactactgtcccctgaagaagtcagtgaaacacaaggaacgg aaaagctgacaataatttattcgtcatcaatgatgtgggagattaatggt cccgaatcagtgttggtcaatacttatcaatggatcatcaggaactggga aattgtaaaaattcagtggtcacaggaccccacaatgttatacaataaga tagaatttgagccattccaatccctggtccctagggccaccagaagccaa tacagcggtttcgtaagaaccctgtttcagcaaatgcgagatgtacttgg aacatttgatactgctcaaataataaaactcctcccttttgccgctgctc ctccggaacagagtaggatgcagttctcttctttgactgttaatgtaaga ggttcgggaatgaggatacttgtaagaggcaattccccagtgttcaacta caataaagccactaaaaggctcacagtcctcggaaaggatgcaggtgcgc ttactgaggacccagatgaaggtacggctggagtagaatctgctgttcta agagggtttctcattttaggtaaagaaaacaagagatatggcccagcact aagcatcaatgaactaagcaaacttgcaaaaggggagaaagccaatgtac taattgggcaaggggacgtagtgttggtaatgaaacggaaacgtgactct agcatacttactgacagccagacagcgaccaaaaggattcggatggccat caattagtgttgaattgtttaaaaacgaccttgtttctact 2. Amino acid sequence of wildtype EIV H3N8 PB2 protein:

(SEQ ID NO: 6)

MERIKELRDLMLQSRTREILTKTTVDHMAIIKKYTSGRQEKNPALRMKWM

MAMKYPITADKRIMEMIPERNEQGQTLWSKTNDAGSDRVMVSPLAVTWWN

RNGPTTSTIHYPKVYKTYFEKVERLKHGTFGPVHFRNQVKIRRRVDVNPG

HADLSAKEAQDVIMEVVFPNEVGARILTSESQLTITKEKKEELQDCKIAP

LMVAYMLERELVRKTRFLPVAGGTSSVYIEVLHLTQGTCWEQMYTPGGEV

RNDDIDQSLIIAARNIVRRATVSADPLASLLEMCHSTQIGGIRMVDILKQ

MPTEEQAVDICKAAMGLRISSSFSFGGFTFKRTSGSSVKREEEMLTGNLQ

TLKIRMHEGYEEFTMVGRRATAILRKATRRLIQLIVSGRDEQSIAEAIIV

AMVFSQEDCMIKAVRGDLNFVNRANQRLNPMHQLLRHFQKDAKVLFQNWG

-continued

IEPIDNVMGMIGILPDMTPSTEMSLRGVRVSKMGVDEYSSTERVVVSIDR

FLRVRDQRGNILLSPEEVSETQGTEKLTIIYSSSMMWEINGPESVLVNTY

QWIIRNWEIVKIQWSQDPTMLYNKIEFEPFQSLVPRATRSQYSGFVRTLF

QQMRDVLGTFDTAQIIKLLPFAAAPPEQSRMQFSSLTVNVRGSGMRILVR

GNSPVFNYNKATKRLTVLGKDAGALTEDPDEGTAGVESAVLRGFLILGKE

NKRYGPALSINELSKLAKGEKANVLIGQGDVVLVMKRKRDSSILTDSQTA

TKRIRMAIN

Wildtype Segment 2 or PB1:

1. Nucleotide sequence of wildtype EIV H3N8 segment 2 (PB1):

(SEQ ID NO: 7)

agcgaaagcaggcaaaccatttgaatggatgtcaatccgactctactttt cttaaaggtgccagcgcaaaatgctataagcacaacattcccttatactg gagatcctccctacagtcatggaacagggacaggatacaccatggatact gtcaacagaacacaccaatattcagaaaaagggaaatggacaacaaacac tgagattggagcaccacaacttaatccaatcgatggaccacttcctgaag acaatgaaccaagtgggtacgcccaaacagattgtgtattggaagcaatg gctttccttgaagaatcccatcccggaatctttgaaaattcgtgtcttga aacgatggaggtgattcagcagacaagagtggacaaactaacacaaggcc gacaaacttatgattggaccttgaataggaatcaacctgccgcaacagca cttgctaatacgattgaagtattcagatcaaatggtctgacttccaatga atcggggagattgatggacttcctcaaagatgtcatggagtccatgaaca aggaagaaatggaaataacaacacacttccaacggaagagaagagtaaga gacaacatgacaaagagaatggtaacacagagaaccatagggaagaagaa acaacgattaaacagaaagagctatctaatcagaacattaaccctaaaca caatgaccaaggacgctgagagagggaaattgaaacgacgagcaatcgct accccagggatgcagataagagggtttgtatattttgttgaaacactagc ccgaagaatatgtgaaaagcttgaacaatcaggattgccagttggcggta atgagaaaaaggccaaactggctaatgtcgtcagaaaaatgatgactaat tcccaagacactgaactctccttcaccatcactggggacaataccaaatg gaatgaaaatcagaacccacgcatattcctggcaatgatcacatacataa ctagaaaccagccagaatggttcagaaatgttctaagcattgcaccgatt atgttctcaaataaaatggcaagactggggaaaggatatatgtttgaaag caaaagtatgaaattgagaactcaaataccagcagaaatgctagcaagca ttgacctgaaatatttcaatgattcaacaaaaaagaaaattgaaaagata cgaccacttctggttgacgggactgcttcactgagtcctggcatgatgat gggaatgttcaacatgttgagcactgtgctgggtgtatccatattaaacc tgggccagaggaaatacacaaagaccacatactggtgggatggtctgcaa tcatccgatgactttgctttgatagtgaatgcgcctaatcatgaaggaat acaagctggagtagacagattctatagaacttgcaaactggtcgggatca acatgagcaaaaagaagtcctacataaatagaactggaacattcgaattc -continued acaagctttttctaccggtatggttttgtagccaatttcagcatggaact acccagttttggggtttccggaataaatgaatctgcagacatgagcattg gagtgacagtcatcaaaaacaacatgataaataatgatctcggtcctgcc acggcacaaatggcactccaactcttcattaaggattatcggtacacata ccggtgccatagaggtgatacccagatacaaaccagaagatcttttgagt tgaagaaactgtgggaacagactcgatcaaagactggtctactggtatca gatgggggtccaaacctatataacatcagaaacctacacatcccggaagt ctgtttaaaatgggagctaatggatgaagattataaggggaggctatgca atccattgaatcctttcgttagtcacaaagaaattgaatcagtcaacagt gcagtagtaatgtctgcgcatggccctgccaaaagcatggagtatgatgc tgttgcaacaacacattcttggatccccaagaggaaccggtccatattga acacaagccaaaggggaatactcgaagatgagcagatgtatcagaaatgc tgcaacctgtttgaaaaattcttccccagcagctcatacagaagaccagt cggaatttctagtatggttgaggccatggtgtccagggcccgcattgatg cacgaattgacttcgaatctggacggataaagaaggatgagttcgctgag atcatgaagatctgttccaccattgaagagctcagacggcaaaaatagtg aatttagcttgatcttcatgaaaaaatgccttgtttctact 2. Amino acid sequence of wildtype EIV H3N8 PB1 protein:

(SEQ ID NO: 8)

MDVNPTLLFLKVPAQNAISTTFPYTGDPPYSHGTGTGYTMDTVNRTHQYS

EKGKWTTNTEIGAPQLNPIDGPLPEDNEPSGYAQTDCVLEAMAFLEESHP

-continued

GIFENSCLETMEVIQQTRVDKLTQGRQTYDWTLNRNQPAATALANTIEVF

RSNGLTSNESGRLMDFLKDVMESMNKEEMEITTHFQRKRRVRDNMTKRMV

TQRTIGKKKQRLNRKSYLIRTLTLNTMTKDAERGKLKRRAIATPGMQIRG

FVYFVETLARRICEKLEQSGLPVGGNEKKAKLANVVRKMMTNSQDTELSF

TITGDNTKWNENQNPRIFLAMITYITRNQPEWFRNVLSIAPIMFSNKMAR

LGKGYMFESKSMKLRTQIPAEMLASIDLKYFNDSTKKKIEKIRPLLVDGT

ASLSPGMMMGMFNMLSTVLGVSILNLGQRKYTKTTYWWDGLQSSDDFALI

VNAPNHEGIQAGVDRFYRTCKLVGINMSKKKSYINRTGTFEFTSFFYRYG

FVANFSMELPSFGVSGINESADMSIGVTVIKNNMINNDLGPATAQMALQL

FIKDYRYTYRCHRGDTQIQTRRSFELKKLWEQTRSKTGLLVSDGGPNLYN

IRNLHIPEVCLKWELMDEDYKGRLCNPLNPFVSHKEIESVNSAVVMSAHG

PAKSMEYDAVATTHSWIPKRNRSILNTSQRGILEDEQMYQKCCNLFEKFF

PSSSYRRPVGISSMVEAMVSRARIDARIDFESGRIKKDEFAEIMKICSTI

EELRRQK

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunological composition comprising an equine live-attenuated influenza virus, wherein the virus comprises one or more mutations in one or more of: segment 1 and segment 2 of the viral genome, wherein:

a) said segment 1 encodes PB2 protein comprising the amino acid sequence set forth in SEQ ID NO: 2 or an amino acid sequence that is at least 90% homologous to the amino acid sequence set forth in SEQ ID NO: 2, with a proviso that the residue at position 265 is serine; and b) said segment 2 encodes PB1 protein comprising the amino acid sequence set forth in SEQ ID NO: 4 or an amino acid sequence that is at least 90% homologous to the amino acid sequence set forth in SEQ ID NO: 4, with a proviso that the amino acid at position 391 is glutamic acid, the amino acid at position 581 is glycine, and the amino acid at position 661 is threonine.

2. The composition of claim 1 wherein said segment 1 encodes PB2 protein comprising the amino acid sequence set forth in SEQ ID NO: 2 or an amino acid sequence that is at least 95% homologous to the amino acid sequence set forth in SEQ ID NO: 2.

3. The composition of claim 1, wherein said segment 1 encodes PB2 protein comprising the amino acid sequence set forth in SEQ ID NO: 2 or an amino acid sequence that is at least 98% homologous to the amino acid sequence set forth in SEQ ID NO: 2.

4. The composition of claim 1, wherein said PB2 protein comprises the amino acid sequence set forth in SEQ ID NO: 2.

5. The composition of claim 1, wherein said segment 2 encodes PB1 protein comprising the amino acid sequence set forth in SEQ ID NO: 4 or an amino acid sequence that is at least 95% homologous to the amino acid sequence set forth in SEQ ID NO: 4.

6. The composition of claim 1, wherein said segment 2 encodes PB1 protein comprising the amino acid sequence set forth in SEQ ID NO: 4 or an amino acid sequence that is at least 98% homologous to the amino acid sequence set forth in SEQ ID NO: 4.

7. The composition of claim 5, wherein said PB1 protein comprises the amino acid sequence set forth in SEQ ID NO: 4.

8. The composition of claim 1, wherein said segment 1 encodes PB2 protein comprising the amino acid sequence set forth in SEQ ID NO: 2 and wherein said segment 2 encodes PB1 protein comprising the amino acid sequence set forth in SEQ ID NO: 4.

9. The composition of claim 1, wherein the virus is derived from H3N8 subtype of equine influenza A virus.

10. The composition of claim 1, wherein the composition is used for the treatment of equine influenza in a subject.

11. The composition of claim 1, wherein the virus is a master donor virus (MDV) expressing mutant EIV H3N8 PB2, mutant EIV H3N8 PB1, and HA and NA of a different EIV strain.

12. A method for inducing an immune response against equine influenza virus in a subject, the method comprising administering to the subject an immunological composition comprising an equine live-attenuated influenza virus, wherein the virus comprises one or more mutations in one or more of segment 1 and segment 2 of the viral genome, wherein:

a) said segment 1 encodes PB2 protein comprising the amino acid sequence set forth in SEQ ID NO: 2 or an amino acid sequence that is at least 90% homologous to the amino acid sequence set forth in SEQ ID NO: 2, with a proviso that the residue at position 265 is serine; and b) said segment 2 encodes PB1 protein comprising the amino acid sequence set forth in SEQ ID NO: 4 or an amino acid sequence that is at least 90% homologous to the amino acid sequence set forth in SEQ ID NO: 4, with a proviso that the amino acid at position 391 is glutamic acid, the amino acid at position 581 is glycine, and the amino acid at position 661 is threonine.

13. The method of claim 12, wherein said segment 1 encodes PB2 protein comprising the amino acid sequence set forth in SEQ ID NO: 2 or an amino acid sequence that is at least 95% homologous to the amino acid sequence set forth in SEQ ID NO: 2.

14. The method of claim 12, wherein said segment 1 encodes PB2 protein comprising the amino acid sequence set forth in SEQ ID NO: 2 or an amino acid sequence that is at least 98% homologous to the amino acid sequence set forth in SEQ ID NO: 2.

15. The method of claim 12, wherein said PB2 protein comprises the amino acid sequence set forth in SEQ ID NO: 2.

16. The method of claim 12, wherein said segment 2 encodes PB1 protein comprising the amino acid sequence set forth in SEQ ID NO: 4 or an amino acid sequence that is at least 95% homologous to the amino acid sequence set forth in SEQ ID NO: 4.

17. The method of claim 16, wherein said segment 2 encodes PB1 protein comprising the amino acid sequence set forth in SEQ ID NO: 4 or an amino acid sequence that is at least 98% homologous to the amino acid sequence set forth in SEQ ID NO: 4.

18. The method of claim 12, wherein said PB1 protein comprises the amino acid sequence set forth in SEQ ID NO: 4.

19. The method of claim 12, wherein the virus comprises SEQ ID NO: 2 and SEQ ID NO: 4.

20. The method of claim 12, wherein the virus is derived from H3N8 subtype of equine influenza A virus.

21. The method of claim 12, wherein the subject does not have equine influenza, and wherein the method induces immunity against equine influenza.

22. The method of claim 12, wherein the subject is infected equine influenza, and wherein the method induces a therapeutic immune response.

23. The method of claim 12, wherein the immunological composition is administered intranasally, intratracheally, orally, intradermally, intramuscularly, intraperitoneally, intravenously, or subcutaneously.

24. The method of claim 12, wherein the subject is a horse.

25. The method of claim 12, wherein the virus is a master donor virus (MDV) expressing mutant EIV H3N8 PB2, mutant EIV H3N8 PB1, and HA and NA of a different EIV strain.

* * * * *

SEQUENCE LISTING

<160> NUMBER OF SEQ ID NOS: 22

<210> SEQ ID NO 1
<211> LENGTH: 2341
<212> TYPE: DNA
<213> ORGANISM: Artificial Sequence
<220> FEATURE:
<223> OTHER INFORMATION: Chemically synthesized - mutant segment 1 based
on A/equine/Ohio/1/2003 H3N8 EIV

<400> SEQUENCE: 1
agcgaaagca ggtcaaatat attcaatatg gagagaataa aagaactgag agatctgatg 60
ttacaatccc gcacccgcga gatactaaca aaaactactg tggaccacat ggccataatc 120
aagaaataca catcaggaag acaagagaag aaccctgcac ttaggatgaa atggatgatg 180
gcaatgaaat acccaatcac ggcagataag aggataatgg agatgattcc tgagagaaat 240
gaacagggac aaaccctttg gagcaaaacg aacgatgctg gctcagaccg cgtaatggta 300
tcacctctgg cagtgacatg gtggaatagg aatggaccaa caacaagcac aattcattat 360
ccaaaagtct acaaaactta ttttgaaaag gttgaaagat tgaaacacgg aacctttggc 420
cccgttcatt ttaggaatca agtcaagata agacgaagag ttgatgtaaa ccctggtcac 480
gcggacctca gtgccaaaga agcacaagat gtgatcatgg aagttgtttt cccaaatgaa 540
gtgggagcca gaattctaac atcggaatca caactaacaa taaccaaaga gaaaaaggaa 600
gaacttcagg actgcaaaat tgctcccttg atggtagcat acatgctaga aagagagttg 660

-continued

```
gtccgaaaaa caaggttcct cccagtagca ggcggaacaa gcagtgtata cattgaagtg    720

ttgcatctga ctcagggaac atgctgggag caaatgtaca ccccaggagg agaagttaga    780

aacgatgata ttgatcaaag tttaattatt gcagcacgat cgatagtgag aagagcaaca    840

gtatcagcag atccactagc atccctactg gaaatgtgcc acagtacaca gattggtgga    900

ataaggatgg tagacatcct taagcagaat ccaacagagg aacaagctgt ggatatatgc    960

aaagcagcaa tgggattgag aattagctca tcattcagct ttggtggatt caccttcaaa   1020

agaacaagtg gatcatcagt caagagagaa gaagaaatgc ttacgggcaa ccttcaaaca   1080

ttgaaaataa gaatgcatga gggctatgaa gaattcacaa tggtcggaag aagagcaaca   1140

gctattctca gaaaggcaac cagaagattg attcaattga tagtaagtgg gagagatgaa   1200

caatcaattg ctgaagcaat aattgtagcc atggtgtttt cgcaagaaga ttgcatgata   1260

aaagcagttc gaggcgattt gaactttgtt aatagagcaa atcagcgttt gaaccccatg   1320

catcaactct tgaggcattt ccaaaaagat gcaaaagtgc ttttccaaaa ttggggaatt   1380

gaacccatcg acaatgtaat ggggatgatt ggaatattgc ctgacatgac cccaagcacc   1440

gagatgtcat tgagaggagt gagagtcagc aaaatgggag tggatgagta ctccagcact   1500

gagagagtgg tggtgagcat tgaccgtttt ttaagagttc gggatcaaag gggaaacata   1560

ctactgtccc ctgaagaagt cagtgaaaca caaggaacgg aaaagctgac aataatttat   1620

tcgtcatcaa tgatgtggga gattaatggt cccgaatcag tgttggtcaa tacttatcaa   1680

tggatcatca ggaactggga aattgtaaaa attcagtggt cacaggaccc cacaatgtta   1740

tacaataaga tagaatttga gccattccaa tccctggtcc ctagggccac cagaagccaa   1800

tacagcggtt tcgtaagaac cctgtttcag caaatgcgag atgtacttgg aacatttgat   1860

actgctcaaa taataaaact cctccctttt gccgctgctc ctccggaaca gagtaggatg   1920

cagttctctt ctttgactgt taatgtaaga ggttcgggaa tgaggatact tgtaagaggc   1980

aattccccag tgttcaacta caataaagcc actaaaaggc tcacagtcct cggaaaggat   2040

gcaggtgcgc ttactgagga cccagatgaa ggtacggctg gagtagaatc tgctgttcta   2100

agagggtttc tcattttagg taaagaaaac aagagatatg gcccagcact aagcatcaat   2160

gaactaagca aacttgcaaa aggggagaaa gccaatgtac taattgggca aggggacgta   2220

gtgttggtaa tgaaacggaa acgtgactct agcatactta ctgacagcca gacagcgacc   2280

aaaaggattc ggatggccat caattagtgt tgaattgttt aaaaacgacc ttgtttctac   2340

t                                                                   2341
```

```
<210> SEQ ID NO 2
<211> LENGTH: 759
<212> TYPE: PRT
<213> ORGANISM: Artificial Sequence
<220> FEATURE:
<223> OTHER INFORMATION: Chemically synthesized - mutant PB2 based on
      A/equine/Ohio/1/2003 H3N8 EIV

<400> SEQUENCE: 2

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
```

-continued

```
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Ser Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Met His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480
```

-continued

```
Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 3
<211> LENGTH: 2341
<212> TYPE: DNA
<213> ORGANISM: Artificial Sequence
<220> FEATURE:
<223> OTHER INFORMATION: Chemically synthesized - mutant segment 2 based
      on A/equine/Ohio/1/2003 H3N8 EIV

<400> SEQUENCE: 3

agcgaaagca ggcaaaccat ttgaatggat gtcaatccga ctctactttt cttaaaggtg      60

ccagcgcaaa atgctataag cacaacattc ccttatactg gagatcctcc ctacagtcat     120

ggaacaggga caggatacac catggatact gtcaacagaa cacaccaata ttcagaaaaa     180

gggaaatgga caacaaacac tgagattgga gcaccacaac ttaatccaat cgatggacca     240

cttcctgaag acaatgaacc aagtgggtac gcccaaacag attgtgtatt ggaagcaatg     300

gctttccttg aagaatccca tcccggaatc tttgaaaatt cgtgtcttga aacgatggag     360

gtgattcagc agacaagagt ggacaaacta acacaaggcc gacaaactta tgattggacc     420
```

-continued ttgaatagga atcaacctgc cgcaacagca cttgctaata cgattgaagt attcagatca 480
aatggtctga cttccaatga atcggggaga ttgatggact tcctcaaaga tgtcatggag 540
tccatgaaca aggaagaaat ggaaataaca acacacttcc aacggaagag aagagtaaga 600
gacaacatga caaagagaat ggtaacacag agaaccatag ggaagaagaa acaacgatta 660
aacagaaaga gctatctaat cagaacatta accctaaaca caatgaccaa ggacgctgag 720
agagggaaat tgaaacgacg agcaatcgct accccaggga tgcagataag agggtttgta 780
tattttgttg aaacactagc ccgaagaata tgtgaaaagc ttgaacaatc aggattgcca 840
gttggcggta atgagaaaaa ggccaaactg gctaatgtcg tcagaaaaat gatgactaat 900
tcccaagaca ctgaactctc cttcaccatc actggggaca ataccaaatg gaatgaaaat 960
cagaacccac gcatattcct ggcaatgatc acatacataa ctagaaacca gccagaatgg 1020
ttcagaaatg ttctaagcat tgcaccgatt atgttctcaa ataaaatggc aagactgggg 1080
aaaggatata tgtttgaaag caaaagtatg aaattgagaa ctcaaatacc agcagaaatg 1140
ctagcaagca ttgacctgaa atatttcaat gattcaacaa aaaagaaaat tgaagaaata 1200
aggcctcttc tggttgacgg gactgcttca ctgagtcctg gcatgatgat gggaatgttc 1260
aacatgttga gcactgtgct gggtgtatcc atattaaacc tgggccagag gaaatacaca 1320
aagaccacat actggtggga tggtctgcaa tcatccgatg actttgcttt gatagtgaat 1380
gcgcctaatc atgaaggaat acaagctgga gtagacagat tctatagaac ttgcaaactg 1440
gtcgggatca acatgagcaa aaagaagtcc tacataaata gaactggaac attcgaattc 1500
acaagctttt tctaccggta tggttttgta gccaatttca gcatggaact acccagtttt 1560
ggggtttccg gaataaatga atctgcagac atgagcattg gagtgacagt catcaaaaac 1620
aacatgataa ataatgatct cggtcctgcc acggcacaaa tggcactcca actcttcatt 1680
aaggattatc ggtacacata ccggtgccat agaggtgata cccagataca aaccagaaga 1740
tcttttgagt tgaagaagct ttgggggcag actcgatcaa agactggtct actggtatca 1800
gatgggggtc caaacctata taacatcaga aacctacaca tcccggaagt ctgtttaaaa 1860
tgggagctaa tggatgaaga ttataagggg aggctatgca atccattgaa tcctttcgtt 1920
agtcacaaag aaattgaatc agtcaacagt gcagtagtaa tgtctgcgca tggccctgcc 1980
aaaagcatgg agtatgatgc tgttactaca acacattctt ggatacccaa gaggaaccgg 2040
tccatattga acacaagcca aaggggaata ctcgaagatg agcagatgta tcagaaatgc 2100
tgcaacctgt ttgaaaaatt cttccccagc agctcataca gaagaccagt cggaatttct 2160
agtatggttg aggccatggt gtccagggcc cgcattgatg cacgaattga cttcgaatct 2220
ggacggataa agaaggatga gttcgctgag atcatgaaga tctgttccac cattgaagag 2280
ctcagacggc aaaaatagtg aatttagctt gatcttcatg aaaaaatgcc ttgtttctac 2340
t 2341

<210> SEQ ID NO 4
<211> LENGTH: 757
<212> TYPE: PRT
<213> ORGANISM: Artificial Sequence
<220> FEATURE:
<223> OTHER INFORMATION: Chemically synthesized - mutant PB1 based on
A/equine/Ohio/1/2003 H3N8 EIV

<400> SEQUENCE: 4

Met Asp Val Asn Pro Thr Leu Leu Phe Leu Lys Val Pro Ala Gln Asn

-continued

```
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Glu Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430
```

-continued

```
Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Gly Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Ser Ala His Gly Pro Ala Lys Ser Met Glu
                645                 650                 655

Tyr Asp Ala Val Thr Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755
```

<210> SEQ ID NO 5
<211> LENGTH: 2341
<212> TYPE: DNA
<213> ORGANISM: Influenza A virus

<400> SEQUENCE: 5

```
agcgaaagca ggtcaaatat attcaatatg gagagaataa aagaactgag agatctgatg      60

ttacaatccc gcacccgcga gatactaaca aaaactactg tggaccacat ggccataatc     120

aagaaataca catcaggaag acaagagaag aaccctgcac ttaggatgaa atggatgatg     180

gcaatgaaat acccaatcac ggcagataag aggataatgg agatgattcc tgagagaaat     240
```

-continued

```
gaacagggac aaaccctttg gagcaaaacg aacgatgctg gctcagaccg cgtaatggta    300
tcacctctgg cagtgacatg gtggaatagg aatggaccaa caacaagcac aattcattat    360
ccaaaagtct acaaaactta ttttgaaaag gttgaaagat tgaaacacgg aacctttggc    420
cccgttcatt ttaggaatca agtcaagata agacgaagag ttgatgtaaa ccctggtcac    480
gcggacctca gtgccaaaga agcacaagat gtgatcatgg aagttgtttt cccaaatgaa    540
gtgggagcca gaattctaac atcggaatca caactaacaa taaccaaaga gaaaaaggaa    600
gaacttcagg actgcaaaat tgctcccttg atggtagcat acatgctaga aagagagttg    660
gtccgaaaaa caaggttcct cccagtagca ggcggaacaa gcagtgtata cattgaagtg    720
ttgcatctga ctcagggaac atgctgggag caaatgtaca ccccaggagg agaagttaga    780
aacgatgata ttgatcaaag tttaattatt gcagcacgga acatagtgag aagagcaaca    840
gtatcagcag atccactagc atccctactg gaaatgtgcc acagtacaca gattggtgga    900
ataaggatgg tagacatcct taagcagaat ccaacagagg aacaagctgt ggatatatgc    960
aaagcagcaa tgggattgag aattagctca tcattcagct ttggtggatt caccttcaaa   1020
agaacaagtg gatcatcagt caagagagaa gaagaaatgc ttacgggcaa ccttcaaaca   1080
ttgaaaataa gaatgcatga gggctatgaa gaattcacaa tggtcggaag aagagcaaca   1140
gctattctca gaaaggcaac cagaagattg attcaattga tagtaagtgg gagagatgaa   1200
caatcaattg ctgaagcaat aattgtagcc atggtgtttt cgcaagaaga ttgcatgata   1260
aaagcagttc gaggcgattt gaactttgtt aatagagcaa atcagcgttt gaaccccatg   1320
catcaactct tgaggcattt ccaaaaagat gcaaaagtgc ttttccaaaa ttggggaatt   1380
gaacccatcg acaatgtaat ggggatgatt ggaatattgc ctgacatgac cccaagcacc   1440
gagatgtcat tgagaggagt gagagtcagc aaaatgggag tggatgagta ctccagcact   1500
gagagagtgg tggtgagcat tgaccgtttt ttaagagttc gggatcaaag ggaaaacata   1560
ctactgtccc ctgaagaagt cagtgaaaca caaggaacgg aaaagctgac aataatttat   1620
tcgtcatcaa tgatgtggga gattaatggt cccgaatcag tgttggtcaa tacttatcaa   1680
tggatcatca ggaactggga aattgtaaaa attcagtggt cacaggaccc cacaatgtta   1740
tacaataaga tagaatttga gccattccaa tccctggtcc ctagggccac cagaagccaa   1800
tacagcggtt tcgtaagaac cctgtttcag caaatgcgag atgtacttgg aacatttgat   1860
actgctcaaa taataaaact cctccctttt gccgctgctc ctccggaaca gagtaggatg   1920
cagttctctt ctttgactgt taatgtaaga ggttcgggaa tgaggatact tgtaagaggc   1980
aattccccag tgttcaacta caataaagcc actaaaaggc tcacagtcct cggaaaggat   2040
gcaggtgcgc ttactgagga cccagatgaa ggtacggctg gagtagaatc tgctgttcta   2100
agagggtttc tcattttagg taaagaaaac aagagatatg gcccagcact aagcatcaat   2160
gaactaagca aacttgcaaa aggggagaaa gccaatgtac taattgggca aggggacgta   2220
gtgttggtaa tgaaacggaa acgtgactct agcatactta ctgacagcca gacagcgacc   2280
aaaaggattc ggatggccat caattagtgt tgaattgttt aaaaacgacc ttgtttctac   2340
t                                                                   2341
```

<210> SEQ ID NO 6
<211> LENGTH: 759
<212> TYPE: PRT
<213> ORGANISM: Influenza A virus

<400> SEQUENCE: 6

```
Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Met His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415
```

-continued

```
Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 7
<211> LENGTH: 2341
<212> TYPE: DNA
<213> ORGANISM: Influenza A virus

<400> SEQUENCE: 7

```
agcgaaagca ggcaaaccat ttgaatggat gtcaatccga ctctactttt cttaaaggtg      60

ccagcgcaaa atgctataag cacaacattc ccttatactg gagatcctcc ctacagtcat     120
```

-continued

```
ggaacaggga caggatacac catggatact gtcaacagaa cacaccaata ttcagaaaaa    180

gggaaatgga caacaaacac tgagattgga gcaccacaac ttaatccaat cgatggacca    240

cttcctgaag acaatgaacc aagtgggtac gcccaaacag attgtgtatt ggaagcaatg    300

gctttccttg aagaatccca tcccggaatc tttgaaaatt cgtgtcttga aacgatggag    360

gtgattcagc agacaagagt ggacaaacta acacaaggcc gacaaactta tgattggacc    420

ttgaatagga atcaacctgc cgcaacagca cttgctaata cgattgaagt attcagatca    480

aatggtctga cttccaatga atcggggaga ttgatggact tcctcaaaga tgtcatggag    540

tccatgaaca aggaagaaat ggaaataaca acacacttcc aacggaagag aagagtaaga    600

gacaacatga caaagagaat ggtaacacag agaaccatag ggaagaagaa acaacgatta    660

aacagaaaga gctatctaat cagaacatta accctaaaca caatgaccaa ggacgctgag    720

agagggaaat tgaaacgacg agcaatcgct accccaggga tgcagataag agggtttgta    780

tattttgttg aaacactagc ccgaagaata tgtgaaaagc ttgaacaatc aggattgcca    840

gttggcggta atgagaaaaa ggccaaactg gctaatgtcg tcagaaaaat gatgactaat    900

tcccaagaca ctgaactctc cttcaccatc actggggaca ataccaaatg gaatgaaaat    960

cagaacccac gcatattcct ggcaatgatc acatacataa ctagaaacca gccagaatgg   1020

ttcagaaatg ttctaagcat tgcaccgatt atgttctcaa ataaaatggc aagactgggg   1080

aaaggatata tgtttgaaag caaaagtatg aaattgagaa ctcaaatacc agcagaaatg   1140

ctagcaagca ttgacctgaa atatttcaat gattcaacaa aaaagaaaat tgaaaagata   1200

cgaccacttc tggttgacgg gactgcttca ctgagtcctg gcatgatgat gggaatgttc   1260

aacatgttga gcactgtgct gggtgtatcc atattaaacc tgggccagag gaaatacaca   1320

aagaccacat actggtggga tggtctgcaa tcatccgatg actttgcttt gatagtgaat   1380

gcgcctaatc atgaaggaat acaagctgga gtagacagat tctatagaac ttgcaaactg   1440

gtcgggatca acatgagcaa aaagaagtcc tacataaata gaactggaac attcgaattc   1500

acaagctttt tctaccggta tggttttgta gccaatttca gcatggaact acccagtttt   1560

ggggtttccg gaataaatga atctgcagac atgagcattg gagtgacagt catcaaaaac   1620

aacatgataa ataatgatct cggtcctgcc acggcacaaa tggcactcca actcttcatt   1680

aaggattatc ggtacacata ccggtgccat agaggtgata cccagataca aaccagaaga   1740

tcttttgagt tgaagaaact gtgggaacag actcgatcaa agactggtct actggtatca   1800

gatgggggtc caaacctata taacatcaga aacctacaca tcccggaagt ctgtttaaaa   1860

tgggagctaa tggatgaaga ttataagggg aggctatgca atccattgaa tcctttcgtt   1920

agtcacaaag aaattgaatc agtcaacagt gcagtagtaa tgtctgcgca tggccctgcc   1980

aaaagcatgg agtatgatgc tgttgcaaca acacattctt ggatccccaa gaggaaccgg   2040

tccatattga acacaagcca aaggggaata ctcgaagatg agcagatgta tcagaaatgc   2100

tgcaacctgt ttgaaaaatt cttccccagc agctcataca gaagaccagt cggaatttct   2160

agtatggttg aggccatggt gtccagggcc cgcattgatg cacgaattga cttcgaatct   2220

ggacggataa agaaggatga gttcgctgag atcatgaaga tctgttccac cattgaagag   2280

ctcagacggc aaaaatagtg aatttagctt gatcttcatg aaaaaatgcc ttgtttctac   2340

t                                                                   2341
```

<210> SEQ ID NO 8
<211> LENGTH: 757

```
<212> TYPE: PRT
<213> ORGANISM: Influenza A virus

<400> SEQUENCE: 8

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400
```

-continued

```
Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Ser Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755
```

```
<210> SEQ ID NO 9
<211> LENGTH: 2233
<212> TYPE: DNA
<213> ORGANISM: Influenza A virus

<400> SEQUENCE: 9

agcgaaagca ggtactgatc caaaatggaa gactttgtgc gacagtgctt caatccaatg     60
```

```
atcgtcgagc ttgcggaaaa ggcaatgaaa gaatatggag aggacccgaa aatcgaaaca    120
aacaaatttg cagcaatatg cactcacttg gaagtctgct tcatgtactc ggatttccac    180
tttattaatg aactgggtga gtcagtggtc atagagtctg gtgacccaaa tgctcttttg    240
aaacacagat ttgaaatcat tgaggggaga gatcgaacaa tggcatggac agtagtaaac    300
agcatctgca acaccacaag agctgaaaaa cctaaatttc ttccagattt atacgactat    360
aaggagaaca gatttgttga aattggtgtg acaaggagag aagttcacat atactacctg    420
gagaaggcca acaaaataaa gtctgagaaa acacatatcc acattttctc atttacagga    480
gaggaaatgg ctacaaaagc ggactatact cttgatgaag agagtagagc caggatcaag    540
accagactat tcactataag acaagaaatg gccagtagag gcctctggga ttcctttcgt    600
cagtccgaga gaggcgaaga gacaattgaa gaaagatttg aaatcacagg gacgatgcgc    660
aagcttgcca attacagtct cccaccgaac ttctccagcc ttgaaaattt tagagtctat    720
gtggatggat tcgaaccgaa cggcttcatt gagagtaagc tttctcaaat gtccaaagaa    780
gtaaatgcca gaatcgaacc attttcaaag acaacacccc gaccactcaa aatgccaggt    840
ggtccaccct gccatcagcg atctaaattc ttgctaatgg atgctctgaa actgagcatt    900
gaggacccaa gtcacgaggg agagggaata ccactatatg atgcaatcaa atgcatgaaa    960
actttctttg gatggaaaga gcccagtatt gttaaaccac atgaaaaggg tataaacccg   1020
aactatctcc aaacttggaa gcaagtatta gaagaaatac aagaccttga gaacgaagaa   1080
aggacccccca agaccaagaa tatgaaaaaa acaagccaat tgaaatgggc actaggtgaa   1140
aatatggcac cagagaaagt ggattttgag gattgtaaag acatcagtga tttaaaacag   1200
tatgacagtg atgagccaga aacaaggtct cttgcaagtt ggattcaaag tgagttcaac   1260
aaagcttgtg agctgacaga ttcaagctgg atagagctcg atgaaattgg ggaggatgtc   1320
gccccaatag aatacattgc gagcatgagg agaaattatt ttactgctga gatttcccat   1380
tgtagagcaa cagaatatat aatgaaagga gtgtacatca acactgctct actcaatgca   1440
tcctgtgctg cgatggatga atttcaatta attccgatga taagtaaatg caggaccaaa   1500
gaagggagaa ggaaaacaaa tttatatgga ttcataataa agggaagatc ccatttaaga   1560
aatgatactg acgtggtgaa ctttgtaagt atggaatttt ctctcactga tccaagattt   1620
gagccacaca aatgggaaaa atactgcgtt ctagaaattg gagacatgct tctaagaact   1680
gctgtaggtc aagtgtcaag acccatgttt ttgtatgtaa ggacaaatgg aacctctaaa   1740
attaaaatga aatggggaat ggaaatgagg cgctgcctcc ttcagtctct gcaacagatt   1800
gaaagcatga tcgaagctga gtcctcggtc aaagaaaagg acatgaccaa agaatttttt   1860
gagaacaaat cagagacatg gcctatagga gagtcccccca aaggagtgga agagggctca   1920
atcgggaagg tttgcaggac cttattagca aaatctgtgt ttaacagttt gtatgcatct   1980
ccacaactgg aagggttttc agctgaatct aggaaattac ttctcattgt tcaggctctt   2040
agggataacc tggaacctgg aacatttgat attgggggt tatatgaatc aattgaggag   2100
tgcctgatta atgatccctg ggttttgctt aatgcatctt ggttcaactc cttccttaca   2160
catgcactga agtagttgtg gcaatgctac tatttgctat ccatactgtc caaaaaagta   2220
ccttgtttct act                                                      2233
```

<210> SEQ ID NO 10
<211> LENGTH: 716
<212> TYPE: PRT

<213> ORGANISM: Influenza A virus

<400> SEQUENCE: 10

Met Glu Asp Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asn Glu Leu Gly Glu Ser Val Val Ile Glu
50 55 60

Ser Gly Asp Pro Asn Ala Leu Leu Lys His Arg Phe Glu Ile Ile Glu
65 70 75 80

Gly Arg Asp Arg Thr Met Ala Trp Thr Val Val Asn Ser Ile Cys Asn
85 90 95

Thr Thr Arg Ala Glu Lys Pro Lys Phe Leu Pro Asp Leu Tyr Asp Tyr
100 105 110

Lys Glu Asn Arg Phe Val Glu Ile Gly Val Thr Arg Arg Glu Val His
115 120 125

Ile Tyr Tyr Leu Glu Lys Ala Asn Lys Ile Lys Ser Glu Lys Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Ser Arg Gly Leu Trp Asp Ser Phe Arg
180 185 190

Gln Ser Glu Arg Gly Glu Glu Thr Ile Glu Glu Arg Phe Glu Ile Thr
195 200 205

Gly Thr Met Arg Lys Leu Ala Asn Tyr Ser Leu Pro Pro Asn Phe Ser
210 215 220

Ser Leu Glu Asn Phe Arg Val Tyr Val Asp Gly Phe Glu Pro Asn Gly
225 230 235 240

Phe Ile Glu Ser Lys Leu Ser Gln Met Ser Lys Glu Val Asn Ala Arg
245 250 255

Ile Glu Pro Phe Ser Lys Thr Thr Pro Arg Pro Leu Lys Met Pro Gly
260 265 270

Gly Pro Pro Cys His Gln Arg Ser Lys Phe Leu Leu Met Asp Ala Leu
275 280 285

Lys Leu Ser Ile Glu Asp Pro Ser His Glu Gly Glu Gly Ile Pro Leu
290 295 300

Tyr Asp Ala Ile Lys Cys Met Lys Thr Phe Phe Gly Trp Lys Glu Pro
305 310 315 320

Ser Ile Val Lys Pro His Glu Lys Gly Ile Asn Pro Asn Tyr Leu Gln
325 330 335

Thr Trp Lys Gln Val Leu Glu Glu Ile Gln Asp Leu Glu Asn Glu Glu
340 345 350

Arg Thr Pro Lys Thr Lys Asn Met Lys Lys Thr Ser Gln Leu Lys Trp
355 360 365

Ala Leu Gly Glu Asn Met Ala Pro Glu Lys Val Asp Phe Glu Asp Cys
370 375 380

Lys Asp Ile Ser Asp Leu Lys Gln Tyr Asp Ser Asp Glu Pro Glu Thr
385 390 395 400

-continued

Arg Ser Leu Ala Ser Trp Ile Gln Ser Glu Phe Asn Lys Ala Cys Glu
405 410 415

Leu Thr Asp Ser Ser Trp Ile Glu Leu Asp Glu Ile Gly Glu Asp Val
420 425 430

Ala Pro Ile Glu Tyr Ile Ala Ser Met Arg Arg Asn Tyr Phe Thr Ala
435 440 445

Glu Ile Ser His Cys Arg Ala Thr Glu Tyr Ile Met Lys Gly Val Tyr
450 455 460

Ile Asn Thr Ala Leu Leu Asn Ala Ser Cys Ala Ala Met Asp Glu Phe
465 470 475 480

Gln Leu Ile Pro Met Ile Ser Lys Cys Arg Thr Lys Glu Gly Arg Arg
485 490 495

Lys Thr Asn Leu Tyr Gly Phe Ile Ile Lys Gly Arg Ser His Leu Arg
500 505 510

Asn Asp Thr Asp Val Val Asn Phe Val Ser Met Glu Phe Ser Leu Thr
515 520 525

Asp Pro Arg Phe Glu Pro His Lys Trp Glu Lys Tyr Cys Val Leu Glu
530 535 540

Ile Gly Asp Met Leu Leu Arg Thr Ala Val Gly Gln Val Ser Arg Pro
545 550 555 560

Met Phe Leu Tyr Val Arg Thr Asn Gly Thr Ser Lys Ile Lys Met Lys
565 570 575

Trp Gly Met Glu Met Arg Arg Cys Leu Leu Gln Ser Leu Gln Gln Ile
580 585 590

Glu Ser Met Ile Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Lys Gly Val Glu Glu Gly Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Asn Leu Glu Pro Gly Thr Phe Asp Ile Gly Gly Leu Tyr Glu
675 680 685

Ser Ile Glu Glu Cys Leu Ile Asn Asp Pro Trp Val Leu Leu Asn Ala
690 695 700

Ser Trp Phe Asn Ser Phe Leu Thr His Ala Leu Lys
705 710 715

<210> SEQ ID NO 11
<211> LENGTH: 1762
<212> TYPE: DNA
<213> ORGANISM: Influenza A virus

<400> SEQUENCE: 11
agcaaaagca ggggatattt ctgtcaatca tgaagacaac cattattttg atactactga 60
cccattgggc ctacagtcaa aacccaatca gtggcaacaa cacagccaca ttgtgtctgg 120
gacgccatgc agtagcaaat ggaacattgg taaaaacaat aagtgatgat caaattgagg 180
tgacaaatgc tacagaatta gttcagagca tttcaacggg gaaaatatgc aacaactcat 240
atagaattct agatggaaga aattgcacat taatagatgc aatgctagga gacccccact 300
gtgacgcctt tcagtatgag aattgggacc tctttataga aagaagcagc gctttcagca 360

-continued

```
attgctaccc atatgacatc cctgactatg catcgctccg atccattgta gcatcctcag    420

gaacattgga attcacagca gagggattca catggacagg tgtcactcaa aacggaataa    480

gtggagcctg caaaagggga tcagccgata gtttctttag ccgactgaat tggctaacaa    540

aatctggaag ctcttacccc acattgaatg tgacaatgcc taacaataaa aatttcgaca    600

agctatacat ctgggggatt catcacccga gctcaaatca agagcagaca aaattgtaca    660

tccaagaatc aggacgagta acagtctcaa caaaaagaag tcaacaaaca ataatcccta    720

acatcggatc tagaccgtgg gtcagaggtc aatcaggcag gataagcata tactggacca    780

ttgtaaaacc tggagatatc ctaatgataa acagtaatgg caacttagtt gcaccgcggg    840

gatattttaa attgaaaaca gggaaaagct ctgtaatgag atcagatgta cccatagaaa    900

tttgtgtgtc tgaatgtatt acaccaaatg gaagcatctc caacgacaag ccattccaaa    960

atgtgaacaa agttacatat ggaaaatgcc ccaagtatat caggcaaaac actttaaagc   1020

tggccactgg gatgaggaat gtaccagaaa agcaaatcag aggaatcttc ggagcaatag   1080

cgggattcat cgaaaacggc tgggaaggaa tggttgatgg gtggtatggg ttccgatatc   1140

aaaactctga aggaacaggg caagctgcag atctaaagag cactcaagca gccatcgacc   1200

agattaatgg aaagttaaac agagtgattg aaagaaccaa tgagaaattc catcaaatag   1260

agaaggaatt ctcagaagta gaaggaagaa ttcaggactt ggagaaatat gtagaagaca   1320

ccaaaataga cctatggtcc tacaatgcag aattgctggt ggctctagaa aatcaacata   1380

caattgactt aacagatgca gaaatgaata aattatttga gaagactaga cgccagttaa   1440

gagaaaacgc agaagacatg ggaggtggat gtttcaagat ttaccacaaa tgtgataatg   1500

catgcattgg atcaataaga aatgggacat atgaccatta catatacaga gatgaagcat   1560

taaacaaccg atttcagatc aaaggtgtag agttgaaatc aggctacaaa gattggatac   1620

tgtggatttc attcgccata tcatgcttct taatttgcgt tgttctattg ggtttcatta   1680

tgtgggcttg ccaaaaaggc aacatcagat gcaacatttg catttgagta aactgatagt   1740

taaaaacacc cttgtttcta ct                                            1762


<210> SEQ ID NO 12
<211> LENGTH: 565
<212> TYPE: PRT
<213> ORGANISM: Influenza A virus

<400> SEQUENCE: 12

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly Arg
            20                  25                  30

His Ala Val Ala Asn Gly Thr Leu Val Lys Thr Ile Ser Asp Asp Gln
        35                  40                  45

Ile Glu Val Thr Asn Ala Thr Glu Leu Val Gln Ser Ile Ser Thr Gly
    50                  55                  60

Lys Ile Cys Asn Asn Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
```

-continued

```
        115                 120                 125

Ser Ser Gly Thr Leu Glu Phe Thr Ala Glu Gly Phe Thr Trp Thr Gly
    130                 135                 140

Val Thr Gln Asn Gly Ile Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
        275                 280                 285

Ile Glu Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540
```

-continued

Val Leu Leu Gly Phe Ile Met Trp Ala Cys Gln Lys Gly Asn Ile Arg
545 550 555 560

Cys Asn Ile Cys Ile
565

<210> SEQ ID NO 13
<211> LENGTH: 1565
<212> TYPE: DNA
<213> ORGANISM: Influenza A virus

<400> SEQUENCE: 13
agcaaaagca gggtagataa tcactcactg agtgacatca aagtcatggc gtctcaaggc 60
accaaacgat cctatgaaca gatggaaact gatggggaac gccagaatgc aactgaaatc 120
agagcatctg tcggaaggat ggtgggagga atcggccggt tttatgttca gatgtgtact 180
gagcttaaac taaacgacca tgaagggcgg ctgattcaga acagcataac aatagaaagg 240
atggtacttt cggcattcga cgaaagaaga aacaagtatc tcgaggagca tcccagtgct 300
gggaaagacc ctaagaaaac gggaggcccg atatacagaa ggaaagatgg gaaatggatg 360
agggaactca tcctccatga taaagaagaa atcatgagaa tctggcgtca ggccaacaat 420
ggtgaagacg ctactgctgg tcttactcat atgatgatct ggcactccaa tctcaatgac 480
accacatacc aaagaacaag ggctcttgtt cggactggga tggatcccag aatgtgctct 540
ctgatgcaag gctcaaccct cccacggaga tctggagccg ctggtgctgc agtaaaaggt 600
gttggaacaa tggtaatgga actcatcaga atgatcaaac gcggaataaa tgatcggaat 660
ttctggagag gtgaaaatgg tcgaagaacc agaattgctt atgaaagaat gtgcaatatc 720
ctcaaaggga aatttcagac agcagcacaa cgggctatga tggaccaggt gagggaaggc 780
cgcaatcctg gaaacgctga gattgaggat ctcattttct tggcacgatc agcacttatt 840
ttgagaggat cagtagccca taaatcatgc ctacctgcct gtgtttatgg ccttgcagta 900
accagtgggt atgactttga gaaggaagga tactctctgg ttggaattga tcctttcaaa 960
ctactccaga acagtcaaat tttcagtcta atcagaccaa aagaaaaccc agcacacaag 1020
agccagttgg tgtggatggc atgccattct gcagcatttg aggacctgag agttttaaat 1080
ttcattagag gaaccaaagt aatcccaaga ggacagttaa caaccagagg agttcaaata 1140
gcttcaaatg aaaacatgga gacaatagat tctagcacac ttgaactgag aagcaaatat 1200
tgggcaataa ggaccagaag cggaggaaac accagtcaac agagagcatc tgcaggacag 1260
ataagtgtgc aacctacttt ctcagtacag agaaatcttc cctttgagag agcaaccatt 1320
atggctgcat tcactggtaa cactgaaggg aggacttccg acatgagaac ggaaatcata 1380
aggatgatgg aaaatgccaa atcagaagat gtgtctttcc aggggcgggg agtcttcgag 1440
ctctcggacg aaaaggcaac gaacccgatc gtgccttcct ttgacatgag caatgaaggg 1500
tcttatttct tcggagacaa tgctgaggag tttgacaatt aaagaaaaat acccttgttt 1560
ctact 1565

<210> SEQ ID NO 14
<211> LENGTH: 498
<212> TYPE: PRT
<213> ORGANISM: Influenza A virus

<400> SEQUENCE: 14

Met Ala Ser Gln Gly Thr Lys Arg Ser Tyr Glu Gln Met Glu Thr Asp
1 5 10 15

-continued

```
Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Thr Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
            340                 345                 350

Ile Pro Arg Gly Gln Leu Thr Thr Arg Gly Val Gln Ile Ala Ser Asn
        355                 360                 365

Glu Asn Met Glu Thr Ile Asp Ser Ser Thr Leu Glu Leu Arg Ser Lys
    370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430
```

-continued

```
Thr Glu Gly Arg Thr Ser Asp Met Arg Thr Glu Ile Ile Arg Met Met
        435                 440                 445

Glu Asn Ala Lys Ser Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Asn


<210> SEQ ID NO 15
<211> LENGTH: 1460
<212> TYPE: DNA
<213> ORGANISM: Influenza A virus

<400> SEQUENCE: 15

agcaaaagca ggagtttaaa atgaatccaa atcaaaagat aatagcaatt ggatttgcat     60

cattggggat attaatcatt aatgtcattc tccatgtagt cagcattata gtaacagtac    120

tggtcctcaa taacaataga acagatctga actgcaaagg gacgatcata agagagtgca    180

atgaaacagt aagagtagaa aaaattactc aatggtataa taccagtaca attaagtaca    240

tagagagacc ttcaaatgaa tactacatga acaacactga accactttgt gaggcccaag    300

gctttgcacc attttccaaa gataatggaa tacgaattgg gtcgagaggc catgtttttg    360

tgataagaga accttttgta tcatgttcgc cctcagaatg tagaaccttt ttcctcacac    420

agggctcatt actcaatgac aaacattcta acggcacagt aaaggaccga agtccgtata    480

ggactttgat gagtgtcaga atagggcaat cacctaatgt atatcaagct aggtttgaat    540

cggtagcatg gtcagcaaca gcatgccatg atggaaaaaa atggatgaca gttggagtca    600

cagggcccga caatcaagca attgcagtag tgaactatgg aggtgttccg gttgatatta    660

ttaattcatg ggcaggggat attttaagaa cccaagaatc atcatgcacc tgcattaaag    720

gagactgtta ttgggtaatg actgatggac cggcaaatag gcaagctaaa tataggatat    780

tcaaagcaaa agatggaaga gtaattggac agactgatat aagtttcaat gggggacaca    840

tagaggagtg ttcttgttac cccaatgaag ggaaggtgga atgcatatgc agggacaatt    900

ggactggaac aaatagacca attctggtaa tatcttctga tctatcgtac acagttggat    960

atttgtgtgc tggcattccc actgacactc ctaggggaga ggatagtcaa ttcacaggct   1020

catgtacaag tcctttggga aataaaggat acggtgtaaa aggtttcggg tttcgacaag   1080

gaactgacgt atgggccgga aggacaatta gtaggacttc aagatcagga ttcgaaataa   1140

taaaaatcag gaatggttgg acacagaaca gtaaagacca aatcaggagg caagtgatta   1200

tcgatgaccc aaattggtca ggatatagcg gttctttcac attgccggtt gaactaacaa   1260

aaaagggatg tttggtcccc tgtttctggg ttgaaatgat tagaggtaaa cctgaagaaa   1320

caacaatatg gacctctagc agctccattg tgatgtgtgg agtagatcat aaaattgcca   1380

gttggtcatg gcacgatgga gctattcttc cctttgacat cgataagatg taatttacga   1440

aaaaactcct tgtttctact                                               1460


<210> SEQ ID NO 16
<211> LENGTH: 470
<212> TYPE: PRT
<213> ORGANISM: Influenza A virus

<400> SEQUENCE: 16
```

-continued

Met Asn Pro Asn Gln Lys Ile Ile Ala Ile Gly Phe Ala Ser Leu Gly
1 5 10 15

Ile Leu Ile Ile Asn Val Ile Leu His Val Val Ser Ile Ile Val Thr
20 25 30

Val Leu Val Leu Asn Asn Asn Arg Thr Asp Leu Asn Cys Lys Gly Thr
35 40 45

Ile Ile Arg Glu Cys Asn Glu Thr Val Arg Val Glu Lys Ile Thr Gln
50 55 60

Trp Tyr Asn Thr Ser Thr Ile Lys Tyr Ile Glu Arg Pro Ser Asn Glu
65 70 75 80

Tyr Tyr Met Asn Asn Thr Glu Pro Leu Cys Glu Ala Gln Gly Phe Ala
85 90 95

Pro Phe Ser Lys Asp Asn Gly Ile Arg Ile Gly Ser Arg Gly His Val
100 105 110

Phe Val Ile Arg Glu Pro Phe Val Ser Cys Ser Pro Ser Glu Cys Arg
115 120 125

Thr Phe Phe Leu Thr Gln Gly Ser Leu Leu Asn Asp Lys His Ser Asn
130 135 140

Gly Thr Val Lys Asp Arg Ser Pro Tyr Arg Thr Leu Met Ser Val Arg
145 150 155 160

Ile Gly Gln Ser Pro Asn Val Tyr Gln Ala Arg Phe Glu Ser Val Ala
165 170 175

Trp Ser Ala Thr Ala Cys His Asp Gly Lys Lys Trp Met Thr Val Gly
180 185 190

Val Thr Gly Pro Asp Asn Gln Ala Ile Ala Val Val Asn Tyr Gly Gly
195 200 205

Val Pro Val Asp Ile Ile Asn Ser Trp Ala Gly Asp Ile Leu Arg Thr
210 215 220

Gln Glu Ser Ser Cys Thr Cys Ile Lys Gly Asp Cys Tyr Trp Val Met
225 230 235 240

Thr Asp Gly Pro Ala Asn Arg Gln Ala Lys Tyr Arg Ile Phe Lys Ala
245 250 255

Lys Asp Gly Arg Val Ile Gly Gln Thr Asp Ile Ser Phe Asn Gly Gly
260 265 270

His Ile Glu Glu Cys Ser Cys Tyr Pro Asn Glu Gly Lys Val Glu Cys
275 280 285

Ile Cys Arg Asp Asn Trp Thr Gly Thr Asn Arg Pro Ile Leu Val Ile
290 295 300

Ser Ser Asp Leu Ser Tyr Thr Val Gly Tyr Leu Cys Ala Gly Ile Pro
305 310 315 320

Thr Asp Thr Pro Arg Gly Glu Asp Ser Gln Phe Thr Gly Ser Cys Thr
325 330 335

Ser Pro Leu Gly Asn Lys Gly Tyr Gly Val Lys Gly Phe Gly Phe Arg
340 345 350

Gln Gly Thr Asp Val Trp Ala Gly Arg Thr Ile Ser Arg Thr Ser Arg
355 360 365

Ser Gly Phe Glu Ile Ile Lys Ile Arg Asn Gly Trp Thr Gln Asn Ser
370 375 380

Lys Asp Gln Ile Arg Arg Gln Val Ile Ile Asp Asp Pro Asn Trp Ser
385 390 395 400

Gly Tyr Ser Gly Ser Phe Thr Leu Pro Val Glu Leu Thr Lys Lys Gly
405 410 415

-continued

Cys Leu Val Pro Cys Phe Trp Val Glu Met Ile Arg Gly Lys Pro Glu
420 425 430

Glu Thr Thr Ile Trp Thr Ser Ser Ser Ser Ile Val Met Cys Gly Val
435 440 445

Asp His Lys Ile Ala Ser Trp Ser Trp His Asp Gly Ala Ile Leu Pro
450 455 460

Phe Asp Ile Asp Lys Met
465 470

<210> SEQ ID NO 17
<211> LENGTH: 1027
<212> TYPE: DNA
<213> ORGANISM: Influenza A virus

<400> SEQUENCE: 17
agcaaaagca ggtagatatt taaagatgag tcttctaacc gaggtcgaaa cgtacgttct 60
ctctatcgta ccatcaggcc ccctcaaagc cgagatcgcg cagagacttg aagatgtctt 120
tgcagggaag aacaccgatc ttgaggcact catggaatgg ctaaagacaa gaccaatcct 180
gtcacctctg actaaaggga ttttaggatt tgtattcacg ctcaccgtgc ccagtgagcg 240
aggactgcag cgtagacgct ttgtccaaaa tgcccttagt ggaaacggag atccaaacaa 300
catggacaga gcagtaaaac tgtacaggaa gcttaaaaga gaaataacat tccatggggc 360
aaaagaggtg gcactcagct attccactgg tgcactagcc agctgcatgg gactcatata 420
caacagaatg ggaactgtta caaccgaagt ggcatttggc ctggtatgcg ccacatgtga 480
acagattgct gattcccagc atcgatctca caggcagatg gtgacaacaa ccaacccatt 540
aatcagacat gaaaacagaa tggtattagc cagtaccacg gctaaagcca tggaacagat 600
ggcaggatcg agtgagcagg cagcagaggc catggaggtt gctagtaggg ctaggcagat 660
ggtacaggca atgagaacca ttgggaccca ccctagctcc agtgccggtt tgaaagatga 720
tctcattgaa aatttacagg cctaccagaa acggatggga gtgcaaatgc agcgattcaa 780
gtgatcctct cgttattgca gcaagtatca ttgggatctt gcacttgata ttgtggattc 840
ttgatcgtct tttcttcaaa ttcatttatc gtcgccttaa atacgggttg aaaagagggc 900
cttctacgga aggagtacct gagtctatga gggaagaata tcggcaggaa cagcagaatg 960
ctgtggatgt tgacgatggt cattttgtca acatagagct ggagtaaaaa actaccttgt 1020
ttctact 1027

<210> SEQ ID NO 18
<211> LENGTH: 252
<212> TYPE: PRT
<213> ORGANISM: Influenza A virus

<400> SEQUENCE: 18

Met Ser Leu Leu Thr Glu Val Glu Thr Tyr Val Leu Ser Ile Val Pro
1 5 10 15

Ser Gly Pro Leu Lys Ala Glu Ile Ala Gln Arg Leu Glu Asp Val Phe
20 25 30

Ala Gly Lys Asn Thr Asp Leu Glu Ala Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Val
65 70 75 80

-continued

```
Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Ile Glu Asn Leu Gln Ala Tyr
225                 230                 235                 240

Gln Lys Arg Met Gly Val Gln Met Gln Arg Phe Lys
                245                 250
```

<210> SEQ ID NO 19
<211> LENGTH: 97
<212> TYPE: PRT
<213> ORGANISM: Influenza A virus

<400> SEQUENCE: 19

```
Met Ser Leu Leu Thr Glu Val Glu Thr Pro Thr Arg Asn Gly Trp Glu
1               5                   10                  15

Cys Lys Cys Ser Asp Ser Ser Asp Pro Leu Val Ile Ala Ala Ser Ile
            20                  25                  30

Ile Gly Ile Leu His Leu Ile Leu Trp Ile Leu Asp Arg Leu Phe Phe
        35                  40                  45

Lys Phe Ile Tyr Arg Arg Leu Lys Tyr Gly Leu Lys Arg Gly Pro Ser
    50                  55                  60

Thr Glu Gly Val Pro Glu Ser Met Arg Glu Glu Tyr Arg Gln Glu Gln
65                  70                  75                  80

Gln Asn Ala Val Asp Val Asp Asp Gly His Phe Val Asn Ile Glu Leu
                85                  90                  95

Glu
```

<210> SEQ ID NO 20
<211> LENGTH: 890
<212> TYPE: DNA
<213> ORGANISM: Influenza A virus

<400> SEQUENCE: 20

```
agcaaaagca gggtgacaaa aacataatgg attccaacac tgtgtcaagc tttcaggtag      60

actgttttct ttggcatgtc cgcaaacgat tcgcagacca agaactgggt gatgccccat     120

tccttgaccg gcttcgccga gaccagaagt ccctaagggg aagaggtagc actcttggtc     180

tggacatcga aacagccact catgcaggaa agcagatagt ggagcagatt ctggaaaagg     240

aatcagatga ggcacttaaa atgaccattg cctctgttcc tacttcacgc tacttaactg     300
```

-continued

```
acatgactct tgatgagatg tcaagagact ggttcatgct catgcccaag caaaaagtaa    360

caggctccct atgtataaga atggaccagg caatcatgga taagaacatc atacttaaag    420

caaactttag tgtgattttc gaaaggctgg aaacactaat actacttaga gccttcaccg    480

aagaaggagc agtcgttggc gaaatttcac cattaccttc tcttccagga catactaatg    540

aggatgtcaa aaatgcaatt ggggtcctca tcggaggact taaatggaat gataatacgg    600

ttagaatctc tgaaactcta cagagattcg cttggagaag cagtcatgag aatgggagac    660

cttcattccc ttcaaagcag aaatgaaaaa tggagagaac aattaagcca gaaatttgaa    720

gaaataagat ggttgattga agaagtgcga catagattga aaaatacaga aaatagtttt    780

gaacaaataa catttatgca agccttacaa ctattgcttg aagtagaaca agagataaga    840

actttctcgt ttcagcttat ttaatgataa aaaacaccct tgtttctact               890
```

<210> SEQ ID NO 21
<211> LENGTH: 219
<212> TYPE: PRT
<213> ORGANISM: Influenza A virus

<400> SEQUENCE: 21

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Leu Lys Met Thr
65                  70                  75                  80

Ile Ala Ser Val Pro Thr Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Ser Lys Gln Lys
    210                 215
```

<210> SEQ ID NO 22
<211> LENGTH: 121
<212> TYPE: PRT
<213> ORGANISM: Influenza A virus

<400> SEQUENCE: 22

```
Met Asp Ser Asn Thr Val Ser Ser Phe Gln Asp Ile Leu Met Arg Met
```

-continued

```
1               5                   10                  15

Ser Lys Met Gln Leu Gly Ser Ser Ser Glu Asp Leu Asn Gly Met Ile
            20                  25                  30

Ile Arg Leu Glu Ser Leu Lys Leu Tyr Arg Asp Ser Leu Gly Glu Ala
        35                  40                  45

Val Met Arg Met Gly Asp Leu His Ser Leu Gln Ser Arg Asn Glu Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Lys Asn Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
        115                 120
```